(12) United States Patent
Acosta et al.

(10) Patent No.: US 9,395,293 B1
(45) Date of Patent: Jul. 19, 2016

(54) HIGH-THROUGHPUT HYPERSPECTRAL IMAGING WITH SUPERIOR RESOLUTION AND OPTICAL SECTIONING

(71) Applicant: Verily Life Sciences LLC, Mountain View, CA (US)

(72) Inventors: Victor Marcel Acosta, Mountain View, CA (US); Adam Backer, Stanford, CA (US); John D. Perreault, Mountain View, CA (US); Daniele Paolo Piponi, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 14/594,956

(22) Filed: Jan. 12, 2015

(51) Int. Cl.
*G01J 3/50* (2006.01)
*G01N 21/25* (2006.01)
*G02B 21/36* (2006.01)
*G01J 3/02* (2006.01)
*G02B 6/293* (2006.01)
(Continued)

(52) U.S. Cl.
CPC .............. *G01N 21/255* (2013.01); *G01J 3/0205* (2013.01); *G02B 21/361* (2013.01); *G01J 3/0229* (2013.01); *G01J 3/502* (2013.01); *G01J 2003/1278* (2013.01); *G01J 2003/468* (2013.01); *G01N 2201/0675* (2013.01); *G01N 2201/06113* (2013.01); *G02B 6/2931* (2013.01)

(58) Field of Classification Search
CPC ... G01J 3/502; G01J 2003/468; G01J 3/0229; G01J 2003/1278; G02B 6/2931
See application file for complete search history.

(56) References Cited

U.S. PATENT DOCUMENTS

| 6,859,275 B2 | 2/2005 | Fateley et al. |
| 7,339,170 B2 | 3/2008 | Deliwala |
| 7,633,616 B2 | 12/2009 | Hing |

(Continued)

FOREIGN PATENT DOCUMENTS

| GB | 359208 A | 1/1961 |
| JP | 563 101818 A | 5/1988 |

OTHER PUBLICATIONS

De Beule et al., "Generation-3 programmable array microscope (PAM) with digital micro-mirror device (DMD)," Proc. SPIE, vol. 7932, (2011).

(Continued)

*Primary Examiner* — Kara E Geisel
*Assistant Examiner* — Shawn Decenzo
(74) *Attorney, Agent, or Firm* — McDonnell Boehnen Hulbert & Berghoff LLP

(57) ABSTRACT

An imaging system includes a light source configured to illuminate a target and a camera configured to image light responsively emitted from the target and reflected from a spatial light modulator (SLM). The imaging system is configured to generate high-resolution, hyperspectral images of the target. The SLM includes a refractive layer that is chromatically dispersive and that has a refractive index that is controllable. The refractive index of the refractive layer can be controlled to vary according to a gradient such that light reflected from the SLM is chromatically dispersed and spectrographic information about the target can be captured using the camera. Such a system could be operated confocally, e.g., by incorporating a micromirror device configured to control a spatial pattern of illumination of the target and to modulate the transmission of light from the target to the camera via the SLM according to a corresponding spatial pattern.

20 Claims, 10 Drawing Sheets

(51) Int. Cl.
*G01J 3/46* (2006.01)
*G01J 3/12* (2006.01)

(56) References Cited

U.S. PATENT DOCUMENTS

| | | | |
|---|---|---|---|
| 8,305,575 B1* | 11/2012 | Goldstein et al. | G01J 3/021 356/326 |
| 8,406,859 B2 | 3/2013 | Zuzak et al. | |
| 8,810,650 B1* | 8/2014 | Neumann | G01J 3/0289 348/142 |
| 2011/0228267 A1 | 9/2011 | Hayashi | |
| 2014/0172324 A1* | 6/2014 | Delon et al. | G01N 21/6458 702/28 |
| 2014/0233028 A1* | 8/2014 | Englund | G01J 3/2823 356/303 |
| 2014/0240514 A1 | 8/2014 | Love et al. | |
| 2015/0177064 A1* | 6/2015 | Wedelsback | G01J 3/04 356/328 |
| 2015/0277092 A1* | 10/2015 | Backer et al. | G02B 21/16 250/237 R |
| 2015/0332081 A1* | 11/2015 | Laforest et al. | G06K 9/0063 382/191 |

OTHER PUBLICATIONS

Cutler et al., "Multicolor quantum dot tracking using a highspeed hyperspectral line-scanning microscope," PLOS One, vol. 8, May 2013.

Boulder Nonlinear Systems, Inc., "Spatial Light Modulators—XY Series," 2013.

Li et al., "Refractiveindex matching between liquid crystals and photopolynners," Journal of the Society for Information Display, vol. 13/12, pp. 10171026 (2005).

Hanley et al., "Three-dimensional spectral imaging by Hadamard transform spectroscopy in a programmable array microscope," Journal of Microscopy, vol. 197, Pt.1, pp. 5-14 (2000).

Texas Instruments, Inc., DLP9500, Product Data, 2013.

Verveer et al., "Theory of confocal fluorescence imaging in the programmable array microscope (PAM)," Journal of Microscopy, vol. 189, Pt. 3, pp. 192-198 (1988).

International Search Report and Written Opinion of International Application No. PCT/US2016/012815 mailed May 10, 2016.

Qing Ye et al., "High-efficiency electrically tunable phase diffraction grating based on a transparent lead magnesium niobate-lead titanite electro-optic ceramic", Optics Letters, Optical Society of America, US, vol. 36, No. 13, Jul. 1, 2011, pp. 2453-2455.

Yanli Zhang et al., "High-efficiency, liquid-crystal-based, controllable diffraction grating", Journal of the Optical Society Df America A, vol. 22, No. 11, Nov. 1, 2005, page 2510.

Sirleto L. et al., "Electro-Optical Switch And Continuously Tunable Filter Based On A Bragg Grating in A Planar Waveguide With a Liquid Crystal Overlayer", Optical Engineering, Soc. Of Photo-Optical Instrumentation Engineers, vol. 41, No. 11, Nov. 1, 2002, pp. 2890-2898.

* cited by examiner

HIGH-THROUGHPUT HYPERSPECTRAL IMAGING WITH SUPERIOR RESOLUTION AND OPTICAL SECTIONING

BACKGROUND

Unless otherwise indicated herein, the materials described in this section are not prior art to the claims in this application and are not admitted to be prior art by inclusion in this section.

A variety of methods exist to image biological tissues or other materials at the micro-scale (i.e., at scales at or smaller than a few micrometers). Such methods can include optical microscopy according to a variety of different illumination schemes and using optical systems configured in a variety of different ways. Samples to be imaged could be broadly illuminated (e.g., in bright-field microscopy), exposed to some structured illumination (e.g., light sheet microscopy), exposed to polarized illumination (e.g., phase contrast microscopy), exposed to illumination at one or more specified points (e.g., confocal microscopy), or illuminated according to some other scheme. Conversely, light can be received and/or focused from the samples to be imaged in a variety of ways; light can be received from a wide field of the sample and focused on an imager, subjected to an aperture (e.g., an aperture corresponding to an aperture used to illuminate the sample as in, e.g., confocal microscopy) before being imaged by an imager or light sensor, or received by some other means. Further, light of different wavelengths can be used to illuminate a sample (e.g., to excite a fluorophore in the sample) and/or light of different wavelengths can be detected from the sample to determine spectrographic information (e.g., emission spectra, excitation spectra, absorbance spectra) about the sample or according to some other application.

SUMMARY

Some embodiments of the present disclosure provide a system including: (i) a light source; (ii) a first camera, wherein the first camera includes a plurality of light-sensitive elements disposed on a focal surface of the first camera; (iii) a spatial light modulator, wherein the spatial light modulator includes a reflective layer disposed beneath a refractive layer, wherein the refractive layer is configured to have a refractive index that varies spatially across the spatial light modulator according to a controllable gradient, wherein at least the direction and magnitude of the controllable gradient are electronically controllable, and wherein the refractive layer is chromatically dispersive; and (iv) an optical system, wherein the optical system is configured to (a) direct light from the light source to a target, (b) direct light emitted from the target in response to the light from the light source toward the spatial light modulator, and (c) direct light emitted from the target and reflected from the spatial light modulator to the first camera such that the focal surface of the first camera is conjugate to a focal surface passing through the target.

Some embodiments of the present disclosure provide a system including: (i) illuminating means configured to emit light; (ii) first imaging means, wherein the first imaging means include a plurality of light-sensitive elements disposed on a focal surface of the first imaging means; (iii) a spatial light modulating means, wherein the spatial light modulating means include a reflective layer disposed beneath a refractive layer, wherein the refractive layer is configured to have a refractive index that varies spatially across the spatial light modulating means according to a controllable gradient, wherein at least the direction and magnitude of the controllable gradient are electronically controllable, and wherein the refractive layer is chromatically dispersive; and (iv) optical means, wherein the optical means are configured to (a) direct light from the illuminating means to a target, (b) direct light emitted from the target in response to the light from the illuminating means toward the spatial light modulating means, and (c) direct light emitted from the target and reflected from the spatial light modulating means to the first imaging means such that the focal surface of the first imaging means is conjugate to a focal surface passing through the target.

Some embodiments of the present disclosure provide a method including: (i) illuminating, by a light source, a target, via an optical system configured to direct light from the light source to the target; (ii) electronically controlling a spatial light modulator during a first period of time such that a refractive layer of the spatial light modulator has a refractive index that varies spatially across the spatial light modulator according to a controllable gradient, wherein the controllable gradient has at least a first specified direction and a first specified magnitude, wherein the spatial light modulator further includes a reflective layer disposed beneath the refractive layer, and wherein the refractive layer is chromatically disperse; (iii) imaging light emitted from the target in response to the light from the light source during the first period of time using a first camera to produce a first image of the target, wherein the first camera includes a plurality of light-sensitive elements disposed on a focal surface of the first camera, wherein the optical system is further configured to direct light emitted from the target in response to the light from the light source toward the spatial light modulator and direct light emitted from the target and reflected from the spatial light modulator to the first camera such that the focal surface of the first camera is conjugate to a focal surface passing through the target; and (iv) determining spectrographic information for a particular region of the target based at least on the first image of the target.

These as well as other aspects, advantages, and alternatives, will become apparent to those of ordinary skill in the art by reading the following detailed description, with reference where appropriate to the accompanying drawings.

DETAILED DESCRIPTION

Figure 1:
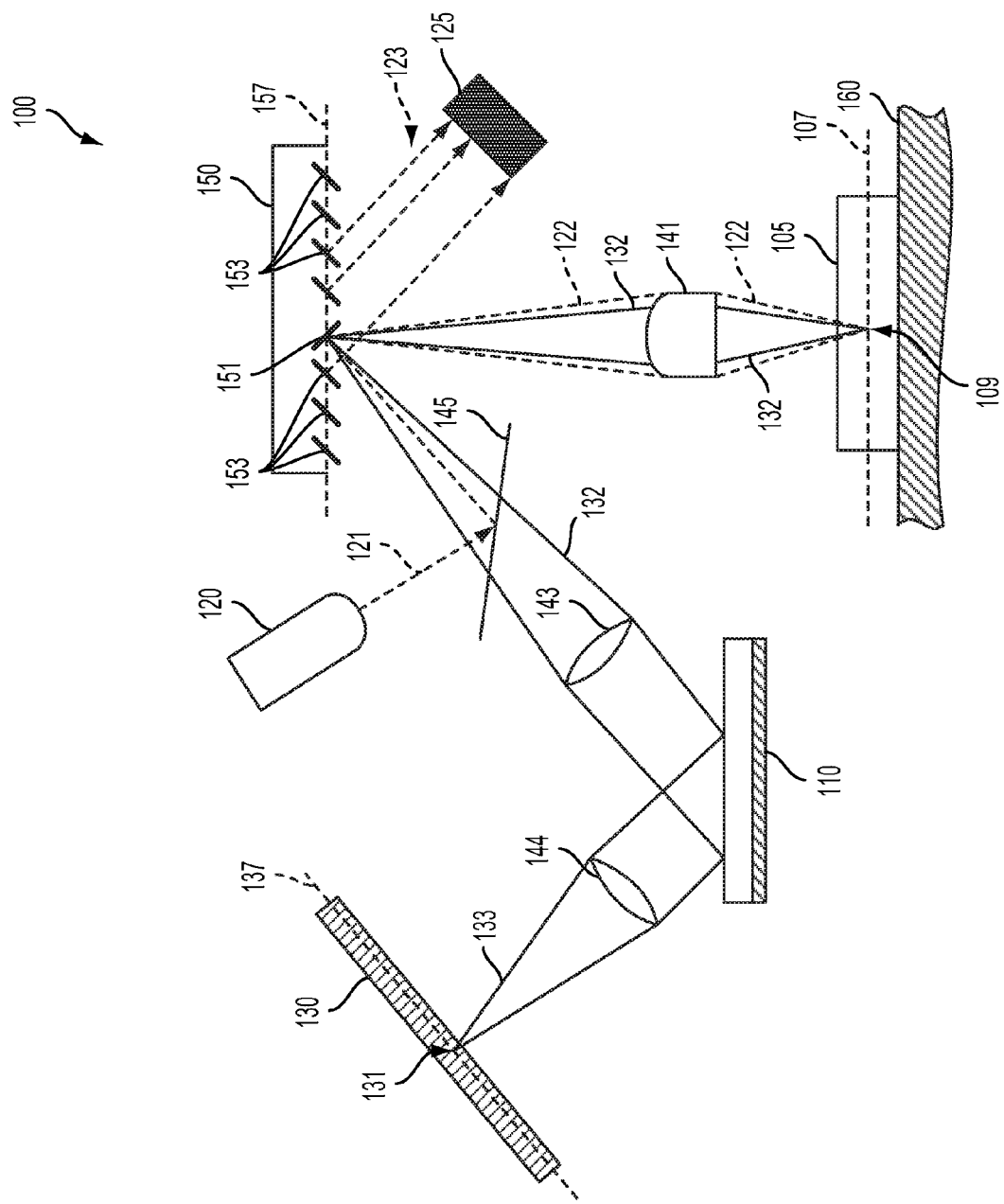
FIG. 1 illustrates an example imaging apparatus.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with samples of tissue extracted from a human body, it is contemplated that the disclosed methods, systems and devices may be used in any environment where spectrographic imaging and/or optical sectioning of other tissues or other objects or elements of an environment is desired. The environment may be any living or non-living body or a portion thereof, a work piece, an implantable device, a mineral, an integrated circuit, a microelectromechanical device, etc.

I. Overview

A variety of microscopy techniques can be applied to determine information about the structure of biological tissues or other materials. Such information can include information about the location, shape, size, or other information about elements of a target (e.g., the location, shape, and/or spectral properties of fluorophores, proteins, cells, or other contents in a sample of biological tissue). These techniques generally include illuminating a target, receiving light responsively emitted from the target, and presenting the received light to a light sensor (e.g., a camera) such that one or more images or other information about the target can be determined.

A variety of optical systems can be used to present illumination to the target (e.g., to present illumination to specified portions of the target) and/or to direct light emitted from the target to a light sensor (e.g., to present light from a focal plane on or within the target to light-sensitive elements arranged on a focal plane of a camera). Systems configured to microscopically image a target can be configured to maximize a spatial resolution (e.g., a minimum resolvable distance between features and/or elements of a target) and/or a temporal resolution (e.g., a rate in time at which images of a target can be generated) of imaging data generated about a target, to minimize an amount of light used to generate images (e.g., to prevent photobleaching or other light-induced effects on a target), or to optimize some other property according to an application.

In some examples, spectrographic information about a target could be detected and/or determined. Spectrographic information could include any information about the dependence of the absorbance, reflectance, excitation, emission, or some other interaction of elements or features of a target with light applied to the target (e.g., visible, infrared, or ultraviolet light) on the wavelength of the applied and/or emitted light. That is, spectrographic information could include one or more of an absorbance spectrum, a reflectance spectrum, an excitation spectrum, an emission spectrum, or some other spectrum detected and/or determined for a plurality of wavelengths. For example, spectrographic information could include a spectrum of light (e.g., a plurality of detected amplitudes corresponding to the amplitudes of light received in a plurality of respective ranges of wavelengths) emitted from a particular portion (e.g., an element or feature) of a target response to illumination of the portion of the target by light (e.g., by monochromatic light).

Such spectrographic information could be accessed by imaging the target using a color camera or otherwise filtering and/or separating light received from the target according to wavelength (e.g., using one or more dielectric mirrors). Additionally or alternatively, light from the target (e.g., from a particular point or other specified portion of the target) could be passed through or otherwise affected by a chromatically dispersive element (e.g., a prism) configured to selectively affect different wavelengths of light (e.g., to reflect and/or refract different wavelength of light at corresponding different angles). For example, a beam of light emitted from a particular portion of a target could be directed through a prism of a spectrometer, and the spectrometer could be operated to determine spectrographic information (e.g., a spectrum) of the beam of light. In some examples, a spatial light modulator could be configured to have one or more electronically controllable optical properties (e.g., a refractive index, a degree of chromatic dispersion) that can be controlled to enable the detection and/or determination of spectrographic information from light received from a target.

In some examples, such a spatial light modulator (SLM) could include a refractive layer disposed on a reflective layer. The refractive layer could be electronically controllable to have a refractive index that varies spatially across a surface of the SLM according to a controllable gradient (e.g., a substantially linear gradient). Further, the controllable refractive index of the refractive layer could be chromatically disperse, i.e., dependent on the wavelength of light refracted by the refractive layer. A magnitude, direction, or other property of the controllable gradient in the refractive index of the SLM could be controlled according to an application, e.g., to control an angle of reflection of light incident on the SLM, to control a degree of spectral dispersion of light reflected from the SLM (e.g., to control a spectral resolution at which an imager receiving the dispersed light could determine spectrographic information for the light reflected form the SLM), or according to some other application.

Spectrographic information could be determined for a particular portion of a target by reflecting a beam of light from the particular portion from such an SLM to a camera. The camera could be operated to detect the intensity of the beam of light at different wavelengths using corresponding different light-sensitive elements of the camera. Additionally or alternatively, a plurality of images of the target could be taken using light reflected from the SLM during a respective periods of time when the SLM is operated to have respective different refractive index patterns (e.g., substantially linear gradients having respective directions and/or magnitudes) and spectrographic information about the target could be determined based on the plurality of images, e.g., by a process of deconvolution.

An SLM could include a chromatically dispersive liquid-crystal layer having refractive index that depends on a magnitude of electrical field or time-varying electrical signal applied to the liquid-crystal. The SLM could include a plurality of electrodes disposed on one or both sides of the liquid-crystal layer such that the refractive index of the SLM could be controlled according to a variety of patterns (e.g., a substantially linear gradient having a specified direction and magnitude). For example, the SLM could have a first transparent electrode opposite the reflective layer and a plurality of regularity-spaced electrodes (e.g., according to a rectangular grid) disposed on or within the reflective layer. Voltages between the first electrode and each of the plurality of regularly-spaced electrodes could be controlled to control the refractive index of corresponding regions (e.g., cells) of the refractive layer disposed between the first electrode and each of the plurality of regularly-spaced electrodes.

A microscope or other imaging system could include such an SLM and be configured to provide hyperspectral confocal imaging, e.g., spatially-sectioned imaging that additionally generates spectrographic information about regions of an imaged target. This could include placing an SLM into the path of light received from a target by a confocal microscope before that light is imaged, e.g., after the received light passes through an aperture (e.g., an aperture that optically corresponds to an aperture through which a light source illuminates the target). In some examples, a system could include an SLM and a micromirror device configured to control a pattern of illumination of a target by a light source. The micromirror device could further control a pattern of light that is received in response from the target and that is presented, via the SLM, to an imager. Such a micromirror device could be controlled to illuminate, and to receive light from, single portions of a target at a time (e.g., by controlling a single micromirror of the micromirror device to reflect illumination from the light source toward a corresponding portion of the target, and conversely to reflect light responsively emitted from corresponding portion of the target, via the SLM, to a camera) and to scan across the target (by sequentially activating particular micromirrors of the micromirror device) to generate a hyperspectral image of the target. Such a micromirror device could additionally or alternatively be operated according to some other method, e.g., to effect a Hadamard or other coded aperture in the reflection of light from the light source to the target or to illuminate a number of spatially separate portions of the target by controlling a corresponding number of spatially separate mirrors of the micromirror device.

Additionally or alternatively, an SLM and corresponding camera could be configured to generate spectrographic information (e.g., hyperspectral images) for a confocally-imaged target using non-conjugate light emitted from the target (i.e., light emitted from portions of the target that do not correspond to apertures of the imaging apparatus that includes the SLM and camera). For example, an imaging system could include a micromirror device, a light source, a first camera, and an optical system configured such that the micromirror device can be operated to control which portion(s) of a target is illuminated by the light source (e.g., by controlling a corresponding micromirror to reflect light from the light source toward the portion of the target) and from which portion(s) light will be reflected toward the first camera, via the micromirror device, to allow the first camera to detect a confocal image of the portion of the target (and of the entire target if the micromirror device is operated to sequentially illuminate different portions of the target, e.g., by operating the micromirrors to scan the illumination across the target). The imaging system is further configured such that light that is not reflected toward the first camera is reflected, in-focus, to a second camera via an SLM. Taking multiple images with both the first and second cameras (e.g., images taken while the micromirror device is operated to sequentially illuminate each portion of the target with light reflected from the light source) could allow for multiple confocal images to be taken of the target (e.g., the multiple images taken by the first camera) and for a single hyperspectral image (or other spectrographic information about the target) to be determined based on the multiple images taken by the second camera (e.g., via a process of deconvolution).

Spectrographic information (e.g., hyperspectral microscopic images) determined about a target using the systems and/or methods herein could be used to enable a variety of applications. Detecting an emission spectrum, excitation spectrum, absorption spectrum, color, or other spectrographic information about elements and/or features of a target could allow for the identification of the elements and/or features of the target (e.g., determining that a feature is a particular protein, based on a correspondence between determined spectrographic information for the feature and known spectrographic information for the particular protein). Additionally or alternatively, one or more properties of an element or feature of the target (e.g., an oxidation state, a local pH, a conformation, a state of binding to a ligand) could be determined based on determined spectrographic information for the element or feature (e.g., based on a center frequency, width, amplitude, shape, or other property of a peak or other feature of a determined absorption, emission, excitation, or other spectrum of the element or feature).

In some examples, spectrographic information determined about a target using the systems and/or methods herein could be used to determine the location, properties, identity, and other information about fluorophores in a target. Such fluorophores could be naturally present in the target or could be introduced via staining, genetic manipulation (e.g., the addition of a green fluorescent protein gene to another gene of interest in an organism), or some other method. Targets could be imaged, and the location of such fluorophores in such targets determined, by illuminating the target with light at an emission wavelength of the fluorophores. Spectrographic information could be determined for the target (e.g., for portions of the target containing such fluorophores) and used to determine the identity of individual fluorophores in the target (e.g., by determining that an emission spectrum of an imaged fluorophore corresponds to the emission spectrum of one of a set of fluorophores present in the target). Additionally or alternatively, information about the state of the fluorophore (e.g., an oxidation state, a local pH, a conformation, a state of binding to a ligand) could be determined based on determined spectrographic information for the fluorophore.

Other configurations, modes and methods of operation, and other embodiments are anticipated. Systems and/or methods described herein could include additional microscopic or other imaging modalities and/or optical systems or elements to improve the identification of the contents of portions of a target according to an application. A system as described herein could include multiple light sources, multiple spatial light modulators, multiple cameras, multiple micromirror devices, and/or additional components according to an application. Systems and methods described herein could be used to add hyperspectral and/or spectrographic imaging capabilities to a variety of other microscopic or other imaging systems. Further, systems and methods as described herein could be configured or operated according to and/or in combination with a variety of different microscopic or other imaging techniques, e.g., stimulated emission depletion, ground state depletion, saturated structured illumination microscopy, 4 pi imaging, photobleaching, or other methods or techniques.

Systems or methods described herein could be applied toward imaging and/or determining spectrographic information about biological tissue or some other type of target. For example, systems and methods described herein could be used to hyperspectrally image materials, alloys, ores, minerals, textiles, microfluidic systems, chemical and/or pharmaceutical products, manufactured nanostructures (e.g., integrated circuits and/or microelectromechanical systems) or other types of targets. Other applications and configurations of systems as described herein are anticipated.

It should be understood that the above embodiments, and other embodiments described herein, are provided for explanatory purposes, and are not intended to be limiting.

II. Example Imaging Apparatus and Example Spatial Light Modulator

A variety of applications include imaging a target (e.g., a biological sample, a mineral, an integrated circuit, a material surface, a surface coating) at a very small scale. In some applications, it could be advantageous to detect spectrographic information about the target, e.g., to detect an excitation spectrum, an emission spectrum, an absorption spectrum, a reflection spectrum, a scattering spectrum, a color, or some other spectrum or other wavelength-dependence of interaction with light of one or more portions (e.g., proteins, cells, or other elements) of the target. Such detected spectrographic information could allow the identification of elements of the target (e.g., by comparing detected spectrographic information from a portion of the target to a database of spectrographic information corresponding to a plurality of potential contents of the target), to allow identification of properties of the target (e.g., to detect a pH in the target based on a detected pH-dependent spectrographic property of one or more elements of the target), or to allow some other application.

Imaging a target at a small scale (e.g., at a scale able to resolve individual features having dimensions less than one micron, or preferentially less than 100 nanometers) could allow for detection of smaller elements or features of the target (e.g., individual cells, individual processes of cells, individual proteins). Imaging the target at a high sample rate (i.e., producing an individual image in a short period of time) could allow the detection of time-dependent processes in the target (e.g., the motion of cell or proteins, changes in the spectrographic properties of a protein due, e.g., to binding and un-binding of the protein with a ligand or analyte). For example, imaging the target at high spatial and temporal resolution (i.e., to resolve very small elements or features of the target during short periods of time) while exposing the target to a minimum of visible light, ultraviolet radiation, infrared radiation, or other illumination may prevent causing damage to the sample and may avoid photobleaching elements (e.g., fluorophores) of the sample.

Imaging a target can include illuminating the target, receiving light responsively emitted from the target (through fluorescent absorption and emission, reflection, scattering, refraction, Raman scattering, or some other interaction between the light and elements of the target), and generating an image of the target based on the received light. Such illumination and/or reception of light can be of/from a wide area of the target (e.g., bright-field microscopy) or of/from some specified region of the target (e.g., a plurality of specified small volumes of the target, as in confocal microscopy). Spectrographic information could be detected/determined for one or more regions of the target by illuminating the target with multiple lights having multiple respective spectrographic properties (e.g., containing light at multiple respective wavelengths) and/or by detecting a wavelength-dependence of the amplitude or other properties of the received light (e.g., by detecting the amplitude of the received light within multiple ranges of wavelengths).

A variety of methods could be employed to determine spectrographic information of light received from a target. In some examples, light received from a target could be filtered and/or reflected according to wavelength (e.g., using a dichroic filter, a dielectric mirror, a gel filter, a Bragg mirror) such that the amplitude or other properties of the received light in one or more specified ranges of wavelengths could be detected. For example, a color camera could include a plurality of red, green, and blue filters configured to filter received light that is directed to respective light-sensitive elements (e.g., pixels) of the camera, allowing the use of the color camera to detect spectrographic information from the received light. In some examples, the received light could be applied to a chromatically dispersive element (i.e., an element having one or more optical properties that are wavelength-dependent) such that portions of the light at different wavelengths could be differently reflected, refracted, absorbed, or otherwise interacted with to allow detection of spectrographic contents of the received light. For example, the received light could be passed through an optical element (e.g., a prism) having a refractive index that is wavelength-dependent, such that different wavelengths of the received light are refracted differently, e.g., in different directions. In some examples, the received light could be transmitted through or reflected from a diffraction grating configured to transmit or reflect light at different wavelengths in different directions, or to separate, filter, or otherwise interact with the light in a wavelength-dependent manner such that spectrographic content of the received light could be detected. Other methods and/or systems could be used to separate, block, filter, or otherwise manipulate light received from a target in order to detect and/or determine spectrographic information about the received light and/or about the target.

FIG. 1 illustrates in cross-section elements of an example imaging system 100 configured to image a target 105. The system 100 includes a light source 120 (e.g., a laser), a camera 130 (illustrated as a plane of light-sensitive elements located on a focal plane 137 of the camera 130), a micromirror device (MD) 150 (in which the micromirrors are located on a focal plane 157), a spatial light modulator (SLM) 110, and an optical system (including an objective 141, first 143 and second 144 relay lenses, a dichroic mirror 145, and an optical sink 125) configured to direct light to and from the target 105 and between the elements of the system 100. The system 100 additionally includes a stage 160 to which the target 105 is mounted. Note that the MD 150 and camera 130 comprise two-dimensional arrays of micromirrors and light-sensitive elements, respectively. Further, note that the optical system (e.g., 141, 143, 144, 145) and SLM 110 are configured to direct light between the target, 105, MD 150, and camera 130 such that locations on the focal surfaces 157, 137 of the MD 150 and camera 130 correspond to respective locations on the focal surface 107 in the target 105.

The system 100 illuminates a specified region 109 on a focal surface 107 in the target 105 by emitting a first illumination 121 from the light source 120 and reflecting the first illumination 121 from the dichroic mirror 145 toward the MD 150. A selected mirror 151 of the MD 150 that has a location on a focal surface 157 of the MD 150 corresponding to the specified region 109 is controlled to reflect the first illumination 121 toward the target 105 as in-focus illumination 122 via the objective 141. Other mirrors 153 of the MD 150 are controlled to reflect the remainder of the first illumination 121 as waste illumination 123 toward the optical sink 125 to be absorbed. As illustrated, a single mirror (151) is controlled to illuminate (and to receive light from) a corresponding region 109 of the target 105; however, additional mirrors (e.g., selected from other mirrors 153) could be operated simultaneously, sequentially, or according to some other scheme to illuminate (and to receive light from) corresponding additional regions of the target 105.

The system 100 receives light (including conjugate light 132) emitted from the specified region 109 in response to illumination via the objective 141. The conjugate light 132 arrives, in-focus, at the selected mirror 151 and is reflected (through the dichroic mirror 145) toward the SLM 110. The first relay lens 143 (and/or some other optical elements of the system 100) collimates the received light and presents the substantially collimated light to the SLM 110. The SLM 100 reflects the conjugate light 132 as spectrally dispersed light 133 toward the second relay lens 144 that is configured to present the spectrally dispersed light 133 in-focus to a specified region 131 on a focal surface 137 of the camera 130 corresponding to the specified region 109 (e.g., to a region of the camera having one or more light-sensitive elements and/or pixels of the camera 130). The SLM 110 is configured and/or operated such that the spectrally dispersed light 133 is spectrally dispersed relative to the conjugate light 132 in a controlled manner such that spectrographic information of the particular region 109 and/or of the conjugate light 132 can be detected or determined. In some examples, the spectrally dispersed light 133 is spectrally dispersed in a manner related to an electronically controlled direction, magnitude, and/or some other property of a spatial gradient in the refractive index of a layer of the SLM 110.

Note that the system 100 and elements thereof shown in FIG. 1 are intended as a non-limiting example of systems and methods as described elsewhere herein for generating hyperspectral or otherwise spectrographic images of a target (e.g., 105). Imaging systems could include more or fewer elements, and could image a target according to similar or different methods. As shown, the system 100 can be operated to image the target 105 confocally; i.e., to illuminate a specified region of the target 109 in-focus and to receive light responsively emitted from the specified region 109 in-focus using the micromirror device 150 (e.g., to control the spatial pattern of light emitted toward and received from the target 105). Illumination could be delivered to the target 105 and light received from the target 105 in different ways and using differently configured elements (e.g., different optics). The target 105 could be illuminated along an optical path separate from the optical path used to receive light responsively emitted from the target 105. For example, illumination could be transmitted through a target before being received to image the target. Particular regions of the target 105 could be illuminated, and light received from such regions, by steering a beam of illumination using one or more controllable mirrors, lenses, diffraction gratings, or other actuated optical elements.

An SLM (e.g., 110) as described herein could be configured and operated as part of a variety of different imaging systems (e.g., bright-field microscopes, 4-pi microscopes, confocal microscopes, fluorescence microscopes, structured illumination microscopes, dark field microscopes, phase contrast microscopes) to provide controlled spectral dispersion of light for a variety of applications (e.g., to allow hyperspectral or otherwise spectrographic imaging of a target). For example, an SLM as described herein could be inserted into the path of light received by some other variety of microscope or imager (e.g., a bright-field microscope). The SLM could be operated to have a plurality of different specified magnitudes and/or directions of refractive index gradient across the SLM during a respective plurality of periods of time, and such an imager could be configured to generate a plurality of images of the received light reflected from the SLM during the plurality of periods of time. In such examples, spectrographic information about a particular portion of a target (e.g., a target from which the received light is received) could be determined based on a plurality of detected amplitudes (or other properties of light) of pixels across the plurality of images according to a model (e.g., a black-box model fitted to calibration data for the imager) or other description of the relationship between the detected amplitudes and spectrographic properties of regions of the target depending on the configuration of the SLM (e.g., via a process of deconvolution performed on the plurality of images and based on a wavelength-dependent point-spread function determined for the imager). Further, an SLM as described herein could be used to control a direction and/or spectral content of a beam of illumination, e.g., to effect a tunable light source in combination with a source of broad-spectrum light and, e.g., an aperture.

The light source 120 could include a variety of light-emitting elements configured to produce illumination 121 having one or more specified properties (e.g., specified wavelength(s)). This could include lasers, light-emitting diodes (LEDs), or other substantially monochromatic light sources. Additionally or alternatively, the light source 120 could include a light emitting element that emits light across a wider range of wavelengths (e.g., an arc lamp). In some examples, this non-monochromatic light could be emitted through one or more filters (e.g., filters including one or more Bragg reflectors, prisms, diffraction gratings, slit apertures, monochromators) configured to only allow the transmission of light within a narrow range of wavelengths. In some examples, the light source 120 could be configured to emit light at a specified wavelength or having some other specified property to excite a fluorophore in the target 105 or to otherwise selectively interact with (e.g., excite, quench, photobleach) one or more elements of the target 120. For example, the illumination 121 could include light at substantially one wavelength (i.e., could contain light of wavelengths within a specified narrow range of wavelengths) corresponding to an excitation wavelength of a fluorophore (e.g., a green fluorescent protein, a dsRED protein) in the target 105.

In some examples, the light source 120 could include a tunable laser or some other light-emitting element(s) controllable to emit light at any of a plurality of different wavelengths (e.g., wavelengths ranging between approximately 400 nanometers and approximately 2.5 micrometers). Such a tunable laser could include an excimer laser, a dye laser, a $CO_2$ laser, a free-electron laser, or some other laser element configured to emit light at a plurality of different, controllable wavelengths. In some examples, the wavelength of the light emitted by such a tunable laser could be controlled by controlling a geometry or size of one or more elements (e.g., a reflector, a resonating cavity) of the tunable laser. In some examples, a Bragg reflector or other element of the light source 120 (e.g., of a tunable laser) could be rotated or otherwise actuated to control the wavelength of light emitted by the light source 120. In some embodiments, the light source 120 could include a plurality of lasers or other sources of substantially monochromatic light configured to emit light at wavelengths corresponding to respective different wavelengths (e.g., excitation wavelengths of respective fluorophores in the target 105), and operation of the light source 120 to emit light of a particular wavelength could include operating the corresponding laser of the light source 120 to emit light at the controlled wavelength. Other configurations and operations of a light source 120 are anticipated.

The camera 130 could include a plurality of light-sensitive elements disposed on the focal surface 137. The light-sensitive elements could be configured to detect the amplitude or other properties of light received by the camera 130 across a broad range of wavelengths (e.g., across a range of wavelengths of light that can be emitted by elements of the target 105, e.g., a range that includes emission wavelengths of one or more fluorophores in the target 105). That is, the camera 130 could be configured to act as broadband monochrome camera, receiving light from the target 105 (via, e.g., the SLM 110, MD 150, and optical system) during a plurality of periods of time and outputting a respective plurality of images related to the absorption, fluorescent re-emission, or other interactions of the target 105 with light (e.g., light of a corresponding plurality of wavelengths) emitted by the light source 120 during a the respective plurality of periods of time. This could include the camera 130 containing a regular two-dimensional (or otherwise arranged) array of light sensitive elements (e.g., photodiodes, phototransistors, pixels of a charge-coupled device (CCD), active pixel sensors) disposed on the focal surface 137 configured such that the output of an individual light sensitive element is related to the amplitude of the light received by the camera 130 from a particular direction and at a particular wavelength (corresponding to a particular portion of the target 105 and the configuration of the SLM 110 and/or MD 150).

Spectrographic information about a particular portion of the target 105 (e.g., 109) could be determined based on a plurality of detected amplitudes (or other properties of light) detected by a particular set of pixels (or other light sensitive elements) of the camera 130 (e.g., pixels proximate to the specified region 131) when the system 100 is operated and/or configured similarly to FIG. 1, i.e., to illuminate and to receive light from a particular region (e.g., 109) of the target 105 (or from a plurality of such specified regions that are spatially separate, such that individual pixels of the camera 130 receive light from only one such region). Additionally or alternatively, a plurality of images could be captured using the camera 130 during respective periods of time when the SLM 110 and MD 150 are operated according to respective different configurations (e.g., different specified magnitudes and/or directions of refractive index gradient across the SLM 110, different sets of controlled angles of the mirrors 151, 153 of the MD 150). In such examples, spectrographic information about a particular portion of the target 105 (e.g., 109) could be determined based on a plurality of detected amplitudes (or other properties of light) detected by a variety of pixels across the plurality of images according to a model (e.g., a black-box model fitted to calibration data for the system 100) or other description of the relationship between the detected amplitudes and spectrographic properties of regions of the target 105 depending on the configuration of the SLM 110 and MD 150 (e.g., via a process of deconvolution performed on the plurality of images and based on a wavelength-dependent point-spread function determined for the system 100). Other configurations and/or operations of the system 100 to enable the detection and/or determination of spectrographic information for one or more regions of a target are anticipated.

Note that the configuration and/or operation of the system 100 to illuminate and to receive light from a specified region 109 on a focal surface 107 of the target 105 is intended as a non-limiting example. Alternatively, a larger and/or differently-shaped region of the target (e.g., a line within the target; substantially the entire target and/or the entire target within a field of view of the imaging system) could be illuminated by operating the mirrors 151, 153 of the MD 150 according to a different set of controlled angles than those illustrated. For example, a plurality of spatially separated regions proximate to the focal surface 107 of the target 105 could be illuminated and imaged simultaneously by controlling a corresponding plurality of spatially separated mirrors of the MD 150 to reflect the first illumination 121 toward the plurality of the regions of the target 105. The mirrors 151, 153 of the MD 150 could be controlled according to some other pattern, e.g., to approximate some other coded aperture on the focal surface 157 of the MD 150. Further, the light source 120 could emit illumination at a controllable wavelength (e.g., illumination that is substantially monochromatic, but having a wavelength that can be altered by operation of the light source) and spectrographic information could be determined for regions of the target 105 based on images of the target 105 generated when the target 105 is illuminated by different wavelengths of light (e.g., to generate a corresponding plurality of emission spectra for the region corresponding to the different wavelengths of illumination).

Further, note that the location of the focal surface 107 within the target 105 could be controlled (e.g., to allow imaging of elements of the target 105 at different depths within the target 105). In some examples, the stage 160 could be actuated relative to other elements of the system 100 (e.g., relative to the objective 141) such that a location of the target 105 in one or more dimensions could be controlled. For example, the stage 160 could be actuated in a direction parallel to the direction of the conjugate illumination 132 (i.e., in the vertical direction of FIG. 1) such that the location (e.g., the depth) of the focal surface 107 within the target 105 could be controlled. In such an example, a plurality of images and/or spectrographic information could be detected/determined of the target 105 when the focal surface 107 is controlled to be at variety of respective locations (e.g., depths) within the target 105, allowing a 3-dimensional image of the target 105 to be generated from the plurality of images and/or spectrographic information. In some examples, the location of the particular region 109 on the focal surface 107 within the target 105 could be controlled by actuating the stage 160 to control the location of the target 105 relative to the system. Actuation of the stage 160 could include one or more piezo elements, servos motors, linear actuators, galvanometers, or other actuators configured to control the location of the stage 160 (and a target 105 mounted on the stage 160) relative to element(s) (e.g., 141) of the system 100.

The imaging system 100 (or other example imaging and/or microscopy systems described herein) could include additional elements or components (not shown). The imaging system 100 could include one or more controllers configured to operate the SLM 110, light source 120, camera 130, MD 150, actuator(s) configured to control the location of the stage 160, and/or other elements of the imaging system 100. The imaging system 100 could include communications devices (wireless radios, wired interfaces) configured to transmit/receive information to/from other systems (e.g., servers, other imaging devices, experimental systems, sample perfusion pumps, optogenetic or other stimulators) to enable functions and applications of the imaging system 100. For example, the imaging system 100 could include an interface configured to present images of the target 105 generated by the imaging system 100. The imaging system 100 could include an interface configured to present information about the imaging system 100 to a user and/or to allow the user to operate the imaging system 100 (e.g., to set a spectrographic resolution, to set a spatial resolution, to set a temporal resolution/imaging sample rate, to set an operational mode (e.g., conjugate or non-conjugate confocal imaging, bright-field imaging, stimulated emission depletion (STED) imaging), so set a maximum emitted illumination power, to set a range of wavelengths of interest).

Additionally or alternatively, the imaging system 100 (or other example imaging systems described herein) could be configured to communicate with another system (e.g., a cellphone, a tablet, a computer, a remote server) and to present a user interface using the remote system. In some examples, the imaging system 100 could be part of another system. For example, the imaging system 100 could be implemented as part of an electrophysiological experimentation system configured to apply optical, electrical, chemical, or other stimuli to a biological sample (e.g., a sample of cultured or extracted neurons). The imaging system 100 could provide information about changes in the configuration of the biological sample in response to stimuli (e.g., by determining spectrographic information about the tissue related to the presence and/or location of calcium in cells of the sample, e.g., by detecting fluorescent properties of calcium indicators in the sample) and/or could provide information to inform to delivery of stimuli. In some examples, the imaging system 100 could include multiple SLMs 110, light sources 120, cameras 130, MDs 150, or other additional components. The imaging system 100 could include sensors and/or be in communication with sensors configured to image other properties of a target environment (e.g., 105). Other configurations, operations, and applications of imaging systems as described herein are anticipated.

Spectrographic information about a biological tissue, cell, organelle, protein, chemical, fluid, fluorophore, mineral, integrated circuit, microelectromechanical device, or other portion of a target could be detected and/or determined by illuminating the portion of the target, detecting light that is emitted from the portion in response to the illumination, and determining some spectrographic information about the received light. Determining spectrographic information could include generating a spectrum (e.g., a reflectance spectrum, an emission spectrum, an absorbance spectrum) from the received light by detecting the a plurality of amplitudes of the received light within a respective plurality of ranges of wavelengths. That is, the spectrographic information could include a plurality of detected and/or determined amplitudes corresponding to wavelengths of the received light, e.g., at specified wavelengths linearly spaced within a range of wavelengths. Such determined spectrographic information could be generated related to the illumination of the target by light of a single wavelength. Alternatively, such spectrographic information could be determined a plurality of times corresponding to illumination of the target during a respective plurality of different periods of time by light of a respective plurality of different single wavelengths.

Spectrographic information could include a description of one or more features of a spectrum or other wavelength-dependent optical properties of the target; for example, spectrographic information could include an absolute or relative amplitude, mean wavelength, width at half maximum, or other descriptive information about a peak or other feature of a spectrum of a portion of a target. Such spectrographic information could be determined based on a determined and/or detected spectrum (e.g., by extracting an amplitude, width, or wavelength location of a peak within a determined and/or detected plurality of detected amplitudes corresponding to wavelengths of light received from the target). Alternatively, such spectrographic information could be determined in other ways, e.g., through an iterative process that includes controlling an SLM to increase a spectral resolution of an imaging system within a range of wavelengths that includes a peak or other feature of interest of a spectrum. Other types of spectrographic information and methods of detecting and/or determining such spectrographic information are anticipated.

In some examples, a fluorophore, chromophore, pigment, dye, coating, or other substance could be added to a target (e.g., a biological sample) according to an application (e.g., to mark one or more proteins, chemicals, or other elements of interest in the target). For example, a fluorophore configured to selectively interact with an analyte (e.g., with an enzyme, protein, marker, or other element expressed by cancer cells) could be introduced into a biological sample such that the analyte could be detected, localized, and/or identified in the sample using methods as described herein. Such identification could be performed to determine the location, distribution, concentration, or other information about the analyte. In some examples, multiple such fluorophores configured to interact with respective analytes could be added to the target. A spectral resolution (e.g., a difference in wavelength between the wavelengths of light corresponding to detected light amplitudes of a spectrum or other detected or determined spectrographic information) of an imager as described herein could be specified to allow identification of the multiple fluorophores. For example, the spectral resolution could be specified such that two or more peaks in a detected spectrum (e.g., an emission spectrum) corresponding to respective two or more fluorophores in the target could be distinguished (allowing, e.g., the determination of which of the two or more fluorophores are present in a particular region of the target). In some examples, one or more of such fluorophores could be already present in the target, e.g., a fluorescent mineral, a fluorescent protein naturally present in a biological sample, a fluorescent protein present in a biological sample due to genetic manipulation of the sample and/or an organism from which the sample is taken.

The identity of an element of a target (e.g., a particular region, a protein, a cell, a mineral, a chemical) could be determined based on features or other information about the spectrographic information determined for the element. For example, the amplitude, center frequency, shape, presence, or other information about a peak in a determined spectrum could indicate that the element comprises a particular fluorescent protein, mineral, chemical, or other substance or structure. In some examples, the identity and/or contents of an element of a target could be determined by applying a classifier, model, or other algorithm to detected or determined spectrographic information for the element. For example, a vector of values representing a determined emission spectrum for the element (e.g., individual values of the vector represent amplitudes of light received from the element within corresponding ranges of wavelengths) could be applied to a k-means, k-nearest neighbor, neural net, support vector machine, decision tree, or other variety of classifier. Other distinctions and/or identifications of regions of a target, based on additional or alternative features of a spectrum of the regions, are anticipated.

Additionally or alternatively, an introduced and/or already-present fluorophore, chromophore, pigment, dye, coating, or other substance could have one or more spectrographic properties (e.g., an amplitude, center wavelength, width, or other property of a peak within an absorption or other spectrum of the introduced substance) that are related to properties (e.g., a temperature, a pH, an osmolality, a strain, a stress, a pressure, a state of binding with a ligand, a conformational state) of one or more regions or elements of a target. For example, a center frequency or amplitude of an emission peak of a fluorophore could be related to a binding state of a protein that includes the fluorophore (e.g., due to quenching of the fluorophore by another aspect of the protein due to a change in conformation of the protein related to binding of the protein to a ligand). In another example, a center frequency or amplitude of an emission peak of a fluorophore could be related to a presence of calcium in the target proximate to the fluorophore (e.g., the fluorophore could include one of fura-2, indo-1, fluo-3, calcium green-1, or some other fluorescent calcium indicator). In such examples, the spectral resolution could be specified such that the related property can be determined and/or determined to a specified resolution by detecting the related spectrographic property. In some examples, such fluorophores could be already present in the target.

An SLM (e.g., 110) as described herein and used to provide hyperspectral imaging and/or the determination of spectrographic data for one or more regions of a target (e.g., 105) has one or more chromatically dispersive properties that are electronically (or otherwise) controllable and that allow the SLM to spectrally disperse light presented to the SLM. A chromatically dispersive property of an object or material is an optical property that has a dependence on the wavelength of light interacting with the object or material. For example, certain glasses have chromatically dispersive refractive indexes in that the refractive indexes of the glasses are different for different wavelengths of light. In another example, certain diffraction gratings have different effective absorbances and/or angles of reflection for different wavelengths of light. Thus, such objects or materials having chromatically dispersive properties can be used to spectrally disperse light, i.e., to interact with light applied to the object or material in a wavelength-dependent manner such that light emitted from the object or material (e.g., reflected from, absorbed by, transmitted through, optically rotated by) has one or more properties (e.g., an angle, an amplitude, an orientation of polarization) that are wavelength-dependent that were substantially not wavelength-dependent in the applied light. As an example, a prism (e.g., a triangular prism) composed of a glass having a chromatically dispersive refractive index could interact with a beam of white light (e.g., a beam containing light at a variety of amplitudes across the visible spectrum) such that light emitted from the prism at a various visible wavelengths is emitted at respective different angles (e.g., as a 'rainbow').

Such chromatically dispersive objects or materials could be applied to detect spectrographic information about light (e.g., light received from a target) by separating, selectively transmitting, or otherwise interacting with light at different wavelengths, allowing the amplitude or other properties of such light at different wavelengths to be independently detected (e.g., by a plurality of respective light-sensitive elements of a camera, spectrometer, or other sensing device) and used to determine spectrographic information (e.g., a vector of values representing the amplitude at a variety of respective different wavelengths, a center frequency, width at half maximum, amplitude, shape, or other properties of a peak or other feature) about the light. Further, electronic control of such chromatically dispersive properties could allow control of one or more properties of the dispersed light, e.g., a mean angle and/or direction of the dispersed light, a degree of angular or other separation of different wavelengths of light (related, e.g., to a spectral resolution of an imager including such electronically controlled dispersive element(s)), a linearity or nonlinearity of the separation of different wavelengths of light, or some other properties of the dispersed light.

Figure 2A:
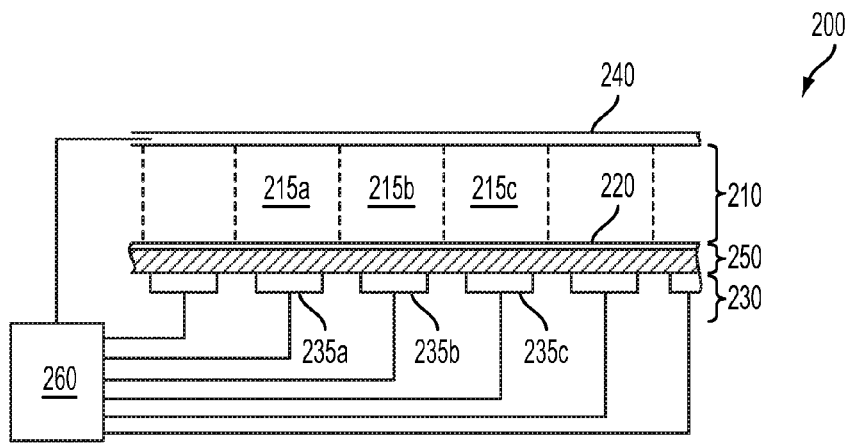
FIG. 2A illustrates a cross-section view of elements of an example spatial light modulator.

An example of such an electronically-controlled chromatically dispersive element is illustrated in cross-section in FIG. 2A. FIG. 2A illustrates the configuration of a spatial light modulator (SLM) 200 that includes a reflective layer 220 (composed of, e.g., aluminum, silver, or some other material that is reflective to light within a range of wavelengths of interest) disposed beneath a refractive layer 210. A substantially transparent first electrode 240 (composed, e.g., of indium-tin-oxide (ITO) or some other material that is electrically conductive and substantially transparent to light within a range of wavelengths of interest) is located on the refractive layer 210 opposite from the reflective layer 220. Light directed toward the SLM 200 could be transmitted through the first electrode 240, refracted by the refractive layer 210, reflected by the reflective layer 220, refracted again by the refractive layer 210, and transmitted away from the SLM 200 through the first electrode 240. The SLM 200 additionally includes a dielectric layer 250 and a plurality of further electrodes 230 (including second 235a, third 235b, and fourth 235c electrodes) disposed beneath the reflective layer 220. A controller 260 is configured to control voltages between the first electrode 240 and each of the further electrodes 230. Note that the reflective layer 220 and dielectric layer 250 are illustrated as distinct structures of the SLM 200, but in practice could be the same structure (e.g., the dielectric layer 250 could be composed of a reflective material such that the reflective layer 220 is simply the surface of the dielectric layer 250, the reflective layer 220 could comprise a polished or otherwise formed or treated surface of the dielectric layer 250 such that the reflective layer 220 is reflective).

The refractive layer 210 is composed of a material (e.g., a liquid crystal) that is chromatically dispersive with respect to its refractive index. That is, the refractive index of the refractive layer 210 depends on the wavelength of light refracted by the refractive layer 210. In some examples, the refractive index of the refractive layer 210 could vary substantially linearly with wavelength for wavelengths within a specified range of wavelengths (e.g., visible wavelengths, a range of wavelengths including emission wavelengths of two or more fluorophores). Further, the refractive index of the refractive layer 210 can be controlled electronically by applying a controlled electric field to the refractive layer 210, e.g., by applying a voltage between the first electrode 240 and one or more of the further electrodes 230. The refractive index of the refractive layer 210 could be related to a linear or nonlinear function of a DC voltage, an amplitude, frequency, duty cycle, pulse width, or other property of an AC voltage, or some other property of voltage applied between the first electrode 240 and one or more of the further electrodes 230. Further, the refractive index of individual regions or cells of the refractive layer 210 could be controlled independently or semi-independently by applying different voltages, voltage waveforms, or other different electronic signals between the first electrode 240 and one or more of the further electrodes 230 corresponding to the individual regions or cells of the refractive layer 210. For example, the refractive index of first 215a, second 215b, and third 215c cells of the refractive layer 210 could be controlled by controlling a voltage or voltage waveform applied between the first electrode 240 and the first 235a, second 235b, and third 235c further electrodes, respectively.

Note that the SLM 200 is illustrated in cross-section in FIG. 2A and thus shows only a single row of cells (e.g., 215a-c) and corresponding electrodes (e.g., 235a-c) of the SLM 200. The SLM 200 could include a regular, two-dimensional array of such cells. Such an array could include a rectangular, square, hexagonal, or other repeating or non-repeating array of such cells and electrodes. Alternatively, an SLM could be configured to have electrodes and corresponding cells or other regions of a refractive layer according to some other pattern or application, e.g., a repeating pattern of linear electrodes (e.g., a 1-dimensional array of cells across the surface of the SLM). The voltages, voltage waveforms, or other electronic signals applied to the electrodes could be controlled such that the refractive index of the refractive layer varies across the surface of the SLM according to a specified pattern, e.g., according to a locally or globally substantially linear or nonlinear gradient. Such a local or global gradient could have a specified magnitude, a specified direction, or some other specified properties. Further, such specified patterns (e.g., gradients) could be changed over time according to some application. For example, light could be received from a target, reflected from such an SLM, and imaged by a camera or other imaging element to allow image capture of light received from a target during a plurality of periods of time when operating the SLM according to respective different patterns (e.g., gradients having respective specified magnitudes and directions) to spectrally disperse the imaged light in a plurality of respective ways, allowing determination of spectrographic information for regions of the target based on the plurality of images, e.g., via a process of deconvolution.

Figure 2B:
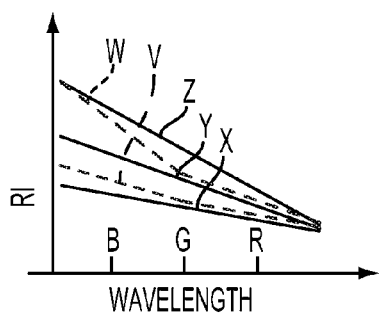
FIG. 2B illustrates the dependence of refractive index on wavelength of light of materials that could be incorporated into the spatial light modulator of FIG. 2A.

FIG. 2B illustrates a variety of functions describing the dependence of the refractive index of portions of the refractive layer 210 (the vertical axis, 'RI') on the wavelength of refracted light (the horizontal axis, 'WAVELENGTH') when composed of different materials and/or when exposed to different electrical fields (e.g., when a specified voltage or voltage waveform is applied between the first electrode 240 and one of further electrodes 230 corresponding to a cell of the SLM 200). 'B', 'G', and 'R' indicate the wavelengths of blue, green, and red light, respectively.

Functions X, Y, and Z illustrate the wavelength-dependent refractive index of a first refractive layer material composition. The first refractive layer material composition has a refractive index that varies substantially linearly across the illustrated range of wavelengths. Functions X, Y, and Z illustrate the refractive index of a cell of the first refractive layer material composition as an applied electronic signal is varied (e.g., X, Y, and Z are the refractive index of the cell as a voltage between electrodes opposite the cell is increased). X, Y, and Z show increasing overall refractive index as well as a decreasing slope of dependence between the refractive index and wavelength. Similarly, functions V and W illustrate the wavelength-dependent refractive index of a second refractive layer material composition; V and W illustrate the refractive index of a cell of the second refractive layer material composition as an applied electronic signal is varied.

Note that the illustrated functions are intended to illustrate configurations and operations of embodiments described herein, and not to limit the embodiments described herein or to describe any particular refractive layer material composition or dependence of optical properties thereof on electronic signals. A refractive index at one or more wavelengths, a slope and/or offset of the refractive index across a range of wavelengths, a nonlinearity of the relationship between the refractive index and wavelength, or some other property of the refractive index of material included in a refractive layer of an SLM as described herein could change linearly or nonlinearly with one or more properties of an applied electrical signal (e.g., an electric field magnitude, an electric field direction, an applied current magnitude, an applied current direction, a frequency, duty cycle, pulse width, or other property of an applied electrical signal).

Figure 2C:
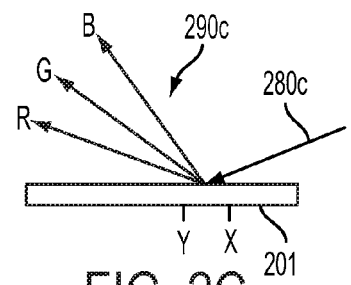
FIG. 2C illustrates reflection of light by the spatial light modulator of FIG. 2A.

FIG. 2C illustrates the use of an SLM 201 configured similarly to SLM 200 and having a refractive layer composed of the first material composition. The SLM 201 is operated such that the refractive layer has a substantially linear gradient of refractive index between the locations indicated by 'X' and 'Y' and such that the locations indicated by 'X' and 'Y' have wavelength-dependent refractive indexes corresponding to the functions 'X' and 'Y', respectively (e.g., by controlling electrodes of cells proximate to 'X' and 'Y' according to corresponding voltages or voltage waveforms and controlling one or more cells located between 'X' and 'Y' according to some intermediate voltages). An incoming light 280c includes light at wavelengths corresponding to the 'R', 'G', and 'B' indications in FIG. 2B. The incoming light 280c is reflected and refracted by the SLM 201 and emitted as reflected light 290c. Due to the wavelength-dependence of the refractive index of the refractive layer of the SLM 201, reflected light 290c is spectrally dispersed (illustrated as separate 'R', 'G', and 'B' rays of light). The angle of each ray of the reflected light 290c could be related to the thickness of the refractive layer of the SLM 201 and the pattern of change of the refractive index of the refractive layer for each ray across the refractive layer. For example, the angle of the 'B' ray could be related to a magnitude and/or angle of a gradient of the refractive index of the refractive layer for light at wavelength 'B' across the SLM 201 in the area proximate the intersection of the SLM 201 and the incoming light 280c.

Figure 2D:
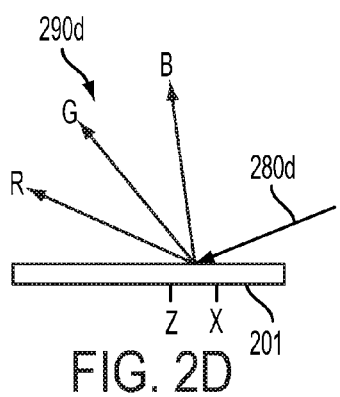
FIG. 2D illustrates reflection of light by the spatial light modulator of FIG. 2A.

An amount of spectral dispersion of light reflected by an SLM could be increased by increasing a magnitude of a gradient or other rate of change in a pattern of the refractive index of the refractive layer. Such an increase in spectral dispersion could allow spectrographic information for a received light to be determined to with a higher spectral resolution, e.g., by causing light of two different wavelengths to be detected by light-sensitive elements (e.g., pixels) of a camera that are farther apart by increasing an angle between rays of dispersed light at the two different wavelengths. As an example, FIG. 2D illustrates the use of the SLM 201 shown in FIG. 2C. The SLM 201 is operated such that the refractive layer has a substantially linear gradient of refractive index between the locations indicated by 'X' and 'Z' and such that the locations indicated by 'X' and 'Z' have wavelength-dependent refractive indexes corresponding to the functions 'X' and 'Z', respectively (e.g., by controlling electrodes of cells proximate to 'X' and 'Z' according to corresponding voltages or voltage waveforms and controlling one or more cells located between 'X' and 'Z' according to some intermediate voltages). An incoming light 280*d* includes light at wavelengths corresponding to the 'R', 'G', and 'B' indications in FIG. 2B. The incoming light 280*d* is reflected and refracted by the SLM 201 and emitted as reflected light 290*d*. Due to the wavelength-dependence of the refractive index of the refractive layer of the SLM 201, reflected light 290*d* is spectrally dispersed. Further, the degree of dispersion of the reflected light 290*d* (e.g., the angular separation between the rays 'R', 'G', and 'B') is increased relative to that shown in FIG. 2C. This could be due to the increased difference in the magnitude of the pattern of change of the refractive index of the refractive layer for each ray across the refractive layer relative to that of the SLM 201 when operated as illustrated in FIG. 2C. For example, the difference in refractive index between points 'X' and 'Z' of FIG. 2D is increased more relative to difference in refractive index between points 'X' and 'Y' of FIG. 2C the for light of shorter wavelengths (e.g., for light at wavelength 'B') than for light of longer wavelengths (e.g., for light at wavelength 'R').

Figure 2E:
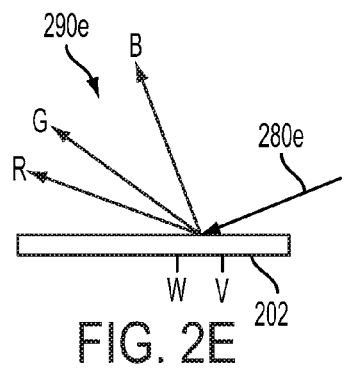
FIG. 2E illustrates reflection of light by the spatial light modulator of FIG. 2A.

An amount of spectral dispersion of light reflected by an SLM could be linear (e.g., a degree of angular separation between spectrally dispersed light at 300 nm and 350 nm could be substantially equal to a degree of angular separation between spectrally dispersed light at 350 nm and 400 nm), nonlinear (e.g., a degree of angular separation between spectrally dispersed light at 300 nm and 350 nm could be greater than a degree of angular separation between spectrally dispersed light at 350 nm and 400 nm), or according to some other relationship related to the composition of refractive and/or reflective elements of the SLM and electrical signal applied to such elements (e.g., to a pattern of voltage applied to cells of such an SLM). As an example, FIG. 2*e* illustrates the use of an SLM 202 configured similarly to SLM 200 and having a refractive layer composed of the second material composition. The SLM 202 is operated such that the refractive layer has a substantially linear gradient of refractive index between the locations indicated by 'V' and 'W' and such that the locations indicated by 'V' and 'W' have wavelength-dependent refractive indexes corresponding to the functions 'V' and 'W', respectively (e.g., by controlling electrodes of cells proximate to 'V' and 'W' according to corresponding voltages or voltage waveforms and controlling one or more cells located between 'V' and 'W' according to some intermediate voltages). An incoming light 280*e* includes light at wavelengths corresponding to the 'R', 'G', and 'B' indications in FIG. 2B. The incoming light 280*e* is reflected and refracted by the SLM 202 and emitted as reflected light 290*e*. Due to the wavelength-dependence of the refractive index of the refractive layer of the SLM 202, reflected light 290*e* is spectrally dispersed. Further, the degree of dispersion of the reflected light 290*e* is not uniform across waveforms. For example, a degree of angular separation between the rays 'R' and 'G' is less than the degree of angular separation between the rays 'G' and 'B'. This could be due to the increased magnitude of change of the refractive index of the refractive layer for each ray owing to the nonlinearity of the functions 'V' and 'W'.

Received light that has been spectrally dispersed by an SLM as described herein (e.g., 280*a*, 280*b*, 280*c* dispersed into 290*c*, 290*d*, 290*e*, respectively) could be applied to an array of light-sensitive elements (e.g., of a camera, as 130) to allow detection of spectrographic information of the received light. In such an example, light of the dispersed light that is at different wavelengths will intersect different light-sensitive elements, such that each light-sensitive element with have an output altered (e.g., increased) by the presence of light at a corresponding wavelength in the received light. In examples wherein the received light comprises a beam that is received from a particular region of a target, a 1-dimensional array of such light-sensitive elements could be used to detect spectrographic information for the particular region by detecting amplitudes (or other properties) of the received light that has been spectrally dispersed by the SLM.

Alternatively, a 2-dimensional array of light sensitive elements could be used. In such examples wherein light is received from a plurality of regions of a target (e.g., as in bright-field microscopy) each light-sensitive element of such a 2-dimensional array could receive light of a variety of different wavelengths from a variety of respective different regions of the target. A correspondence between individual light-sensitive element of such an array to light of a range of regions of a target at a range of corresponding wavelengths could be determined (e.g., by modeling or simulation of elements of such an imaging system, by empirical testing of such a system using one or more calibration targets having respective known patterns of spectrographic properties) and such a correspondence could be used to determine spectrographic information for one or more regions of an imaged target based on a number of images of the target taken while operating the SLM according or a respective number of different patterns of refractive index (e.g., via a process of deconvolution). Such multiple patterns of refractive index across the SLM could include gradients having multiple respective specified magnitudes, directions, or other properties.

Figure 3A:
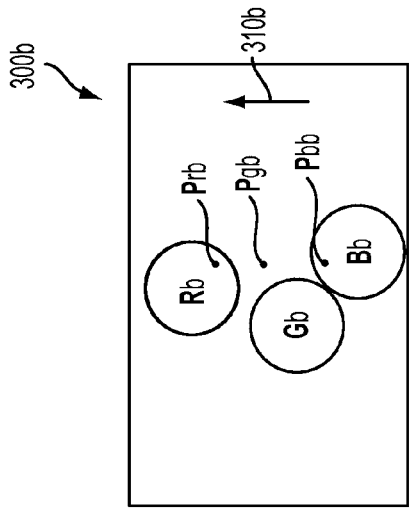
FIG. 3A illustrates an example environment that could be imaged.

FIG. 3A illustrates a target 300*a*. Spectrographic properties of regions of the target 300*a* are such that red region Ra contains fluorophores that emit red light in response to illumination, green region Ga contains fluorophores that emit green light in response to illumination, and blue region Ba contains fluorophores that emit blue light in response to illumination. The target 300*a* could be imaged by an imaging system as described herein, e.g., by system 100 operated such that all of the mirrors (e.g., 151, 153) of the MD 150 are controlled to reflect first illumination 121 toward the target 300*a* (such that, e.g., the whole area of the target 300*a* is illuminated) and to reflect light responsively emitted from the target 300*a*, via reflection from the SLM 110, toward the camera 130 such that the light-sensitive elements of the camera 130 can be operated to image the light received from the target 300*a* and spectrally dispersed by the SLM 110.

Figure 3B:
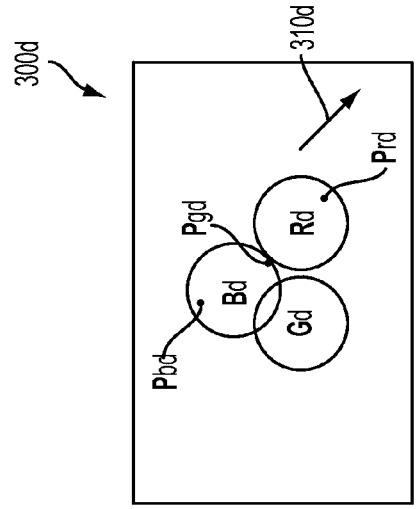
FIG. 3B illustrates an example image of the environment of FIG. 3A.

FIG. 3B illustrates a portion of a first image 300*b* of the target 300*a*. This first image 300*b* is taken of light received from the target that has been spectrally dispersed by an SLM (e.g., 110, 200, 201, 202) during a first period of time. The first image 300*b* includes illuminated regions Rb, Gb, and Bb due to illumination of corresponding regions of a camera by dispersed light from the red, green, and blue regions (Ra, Ga, and Ba), respectively, of the target 300*a*. The SLM is operated during the first period of time such that its refractive layer has a refractive index that varies spatially across the SLM according to a gradient in a first direction (indicated by the arrow 310*b*) such that light of different wavelengths is dispersed in the first direction 310*b* when imaged by a camera (e.g., as in the first image 300*b*). Such dispersion affects imaging of the dispersed light during the first period of time by shifting light at longer wavelengths farther in the direction of the arrow within the first image 300*b*; as a result, the first image 300*b* of the target 300*a* includes illuminated regions Rb, Gb, and Bb arranged as shown.

Figure 3C:
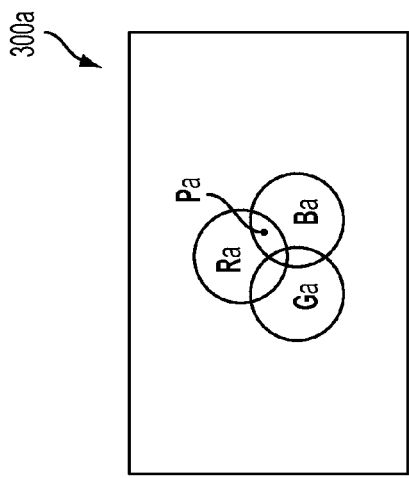
FIG. 3C illustrates an example image of the environment of FIG. 3A.
Figure 3D:
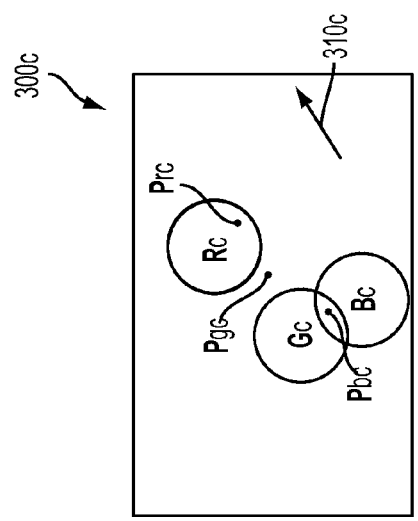
FIG. 3D illustrates an example image of the environment of FIG. 3A.

An imaging system (e.g., 100) could be operated in this way during a plurality of further periods of time to generate a further plurality of respective images of light received from the target and dispersed by the SLM. The SLM could be operated during such further periods of time to such that its refractive layer has a refractive index that varies spatially across the SLM according to respective gradients in respective further directions and/or having respective further magnitudes or according to some other set or respective patterns. FIGS. 3C and 3D illustrate portions of a second image 300c and a third image 300d, respectively, of the target 300a. The second image 300c and third image 300d are taken of light received from the target that has been spectrally dispersed by the SLM during respective second and third periods of time. The second image 300c and third image 300d include respective sets of illuminated regions Rc, Gc, and Bc and Rd, Gd, and Bd due to illumination of corresponding regions of the camera by dispersed light from the red, green, and blue regions (Ra, Ga, and Ba), respectively, of the target 300a.

The SLM is operated during the second and third periods of time such that its refractive layer has a refractive index that varies spatially across the SLM according to a gradient in a second direction and a third direction, respectively (indicated by the arrows 310c, 310d, respectively) such that light of different wavelengths is dispersed in the second direction 310c and third direction 310d when imaged during the second and third periods of time by the camera (e.g., as in the second 300c and third 300d images). Such dispersion affects imaging of the dispersed light during the second and third periods of time by shifting light at longer wavelengths farther in the direction of respective arrows within the second 300c and third 300d images. As a result, the second image 300c of the target 300a includes illuminated regions Rc, Gc, and Bc and the third image 300d of the target 300a includes illuminated regions Rd, Gd, and Bd arranged as shown. Note that, in this illustrative example, overlapping regions in the images (e.g., the region of overlap between Gc and Bc in the second image 300c, the region of overlap between Gd and Bd in the third image 300d) could be represented by an increased measured intensity or other increased detected property of the dispersed light due to receiving light from both the green region Ga and blue region Ba of the target 300a Such multiple images of the target 300a, taken from light dispersed in respective multiple ways by the SLM operated according to respective multiple configurations of refractive index (e.g., according to gradients having respective different directions and/or magnitudes) could be used to determine spectrographic information for one or more regions (e.g., particular region Pa) of the target 300a. In some examples, such information could be determined for a plurality of regions across the target 300a allowing, e.g., hyperspectral imaging of the target 300a. A plurality of such images, in combination with a model or other algorithm describing the effects of the plurality of patterns of refractive index of the SLM and/or the effects of such configurations to disperse light received from the target 300a during the periods of time corresponding to the plurality of images. Such a determination could include a process of deconvolution or some other computational process.

In an illustrative example, spectrographic information about the particular region Pa of the target 300a could be determined based on the amplitude or other detected information about light detected at regions of the camera (e.g., by one or more light-sensitive elements or pixels of the camera) corresponding, according to the location of the particular region Pa and the dispersive effects of the SLM during the plurality of periods of time corresponding to the plurality of images. For example, an amplitude of red light emitted from Pa in response to illumination by the imaging system could be determined based on a linear combination or other function of the light detected at points Prb, Prc, and Prd in the first 300a, second 300b, and third 300c images of the target. Similarly, an amplitude of green light emitted from Pa in response to illumination by the imaging system could be determined based on a linear combination or other function of the light detected at points Pgb, Pgc, and Pgd in the first 300a, second 300b, and third 300c images of the target and an amplitude of blue light emitted from Pa in response to illumination by the imaging system could be determined based on a linear combination or other function of the light detected at points Pbb, Pbc, and Pbd in the first 300a, second 300b, and third 300c images of the target.

The location of such corresponding locations (e.g., Prb, Prc, Prd, Pgb, Pgc, Pgd, Pbb, Pbc, Pbd) could be determined based on a model of the imager (e.g., based on the magnitude and direction of a gradient of refractive index of the refractive layer across the SLM) and/or on an empirical measurement of the properties of the imager (e.g., based on a set of images of a calibration target having known spectrographic information/content or some other calibration information or procedure). Note that the colors (red, green, and blue) and operation of the SLM to disperse light in the illustrated different directions are intended as non-limiting examples; different wavelengths and/or ranges of wavelengths of spectrographic information could be determined for regions of a target. Further, an SLM could be operated to have a pattern of refractive index according to gradients having respective different directions, magnitudes, or according to some other set of patterns of refractive index.

A spectral and/or spatial resolution of such determined spectrographic information could be increased by capturing more images of the target 300a while operating the SLM to have respective different patterns of refractive index (e.g., gradients having respective different magnitudes and directions, other patterns). Such patterns could include substantially linear gradients across the entire refractive layer of the SLM, patterns having a variety of local gradients (themselves having respective magnitudes and/or directions) in refractive index, or some other random or pseudo-random patterns of refractive index according to an application. Additionally or alternatively, a magnitude of a gradient in such a pattern or refractive index of an SLM could be increased to increase a spectral resolution of such determined spectrographic information. Further, such a gradient magnitude could be adaptively adjusted, e.g., to allow two or more peaks (e.g., corresponding to respective two or more fluorophores in a target) in an emission or other spectrum of received light to be distinguished.

Note that the described regular array of electrodes disposed as part of an SLM to allow the electronic control of the refractive index of respective cells or other specified regions of a refractive layer (or other refractive element(s)) of the SLM is intended as one example embodiment of an SLM having a refractive layer having a refractive index that can be electronically controlled to vary across the refractive layer according to a controllable gradient having at least one of a specified direction or magnitude. Alternative embodiments could electronically control one or more lasers or other light sources to optically control the refractive index of a refractive element of an SLM. Other configurations and operations of an SLM as described herein are anticipated. Further, an SLM could be operated in a transmissive mode, i.e., could lack a reflective layer. In such examples, a beam of light (e.g., a beam of light received from an illuminated target) could be spectrally dispersed by the SLM by being transmitted through a refractive layer of the SLM that has a pattern of refractive index that can be electronically controlled. In some examples, an SLM could act to provide electronically controlled spectral dispersion of a beam of light by controlling a pattern of reflective and absorptive elements on a surface and/or within a volume of the SLM to provide a diffraction grating having one or more properties (e.g., a grating spacing, a grating width, a grating orientation) that can be electronically controlled to control one or more properties of spectrally dispersed light reflected from and/or transmitted through the SLM in response to receiving light from a target.

Other methods of configuring and/or operating a light source, camera, SLM, MD, and/or other elements of an imaging system (e.g., to identify one or more regions of a target, to photobleach or otherwise interact with the region of the target based on such identification) are anticipated.

III. Example Confocal Operation of an Imaging Apparatus and Example Micromirror Device Imaging devices as described herein (i.e., imaging devices including one or more spatial light modulator (SLMs) configured and/or operated as described herein to spectrally disperse light received from a target in an electronically controllable manner) could be configured in a variety of ways to effect imaging of a target through a variety of methods. Such methods could include illuminating and/or receiving light from the target according to a variety of patterns (e.g., illuminating and receiving light from a broad area of the target at once as in bright-field microscopy, illuminating and receiving light from a single point or a small set of points at a time as in confocal microscopy or some other sort of scanning microscopy). Further, light from a single region (or set of spatially distinct regions) of the target could be spectrally dispersed by an SLM and the dispersed light imaged, light from a broad region of the target could be dispersed by an SLM and the dispersed light imaged, or light from the target and/or some specified region(s) of the target could be spectrally dispersed and/or imaged according to some other method or combination of methods.

In some examples (e.g., the system 100 illustrated in FIG. 1) one or more specified regions of a target could be illuminated. Similarly, light responsively emitted from such specified regions, or additional or alternative regions of a target, could be collected, focused, or otherwise received, spectrally dispersed, and detected (e.g., by light-sensitive elements of a camera) to determine spectrographic information for the specified regions and/or for the target as a whole (e.g., to generate a hyperspectral image of the target). An imaging system could be configured in a variety of ways to illuminate and/or to receive light from one or more specified regions of a target. For example, illumination could be delivered to a specified region of the target through an aperture and/or from a point source of light. An imaging system could include an optical system configured to direct such light to a specified region of the target such that the aperture and/or point source is located at a location that is conjugate (i.e., such that the light is delivered in-focus to the specified region, as in FIG. 1) to the location of the specified region. Conversely, light received from the specified region of the target could be received, in-focus, via such an aperture and/or via a different aperture that has a location that is conjugate to the location of the specified region.

The location of one or more specified regions to illuminate and/or receive light from could be controlled by controlling the location of the target relating to one or more elements (e.g., an objective) of an imaging system (e.g., by controlling the location of an actuated stage to which a biological sample or other target is mounted). Additionally or alternatively, the location of an aperture through which illumination is emitted and/or through which light responsively emitted from a target could be received could be controlled (e.g., scanned across a range of locations corresponding to locations on or within the target). For example, one or more apertures could be formed as part of a Nipkow disk or some other image scanning apparatus. In some examples, a pattern of such apertures could be programmed into the configuration of a spatial light modulator (e.g., a pattern of opacity of cells of a transmissive-mode spatial light modulator, a pattern of controlled angles of micromirrors of a micromirror device as in, e.g., FIG. 1).

Figure 4A:
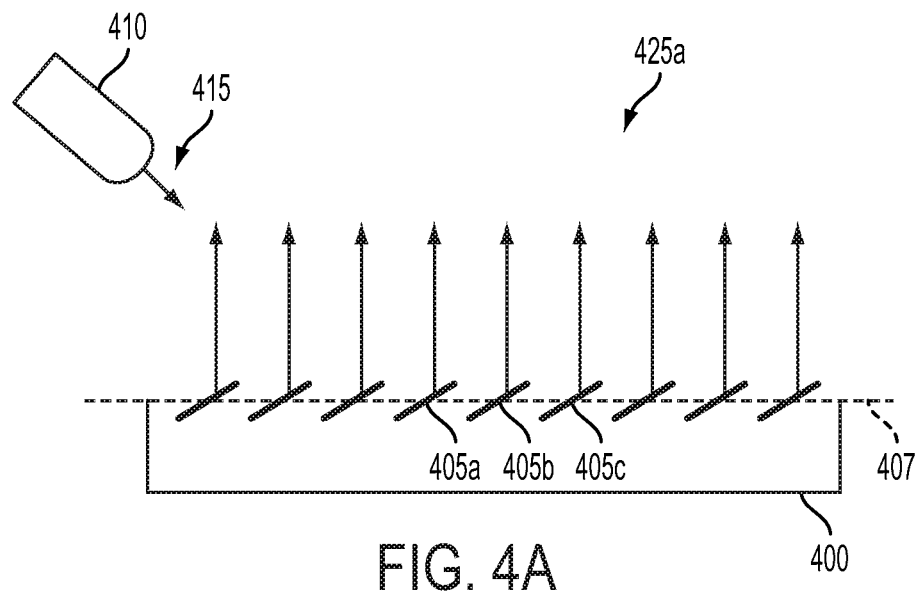
FIG. 4A illustrates a cross-section view of elements of an example micromirror device reflecting laser light during a first period of time.
Figure 4B:
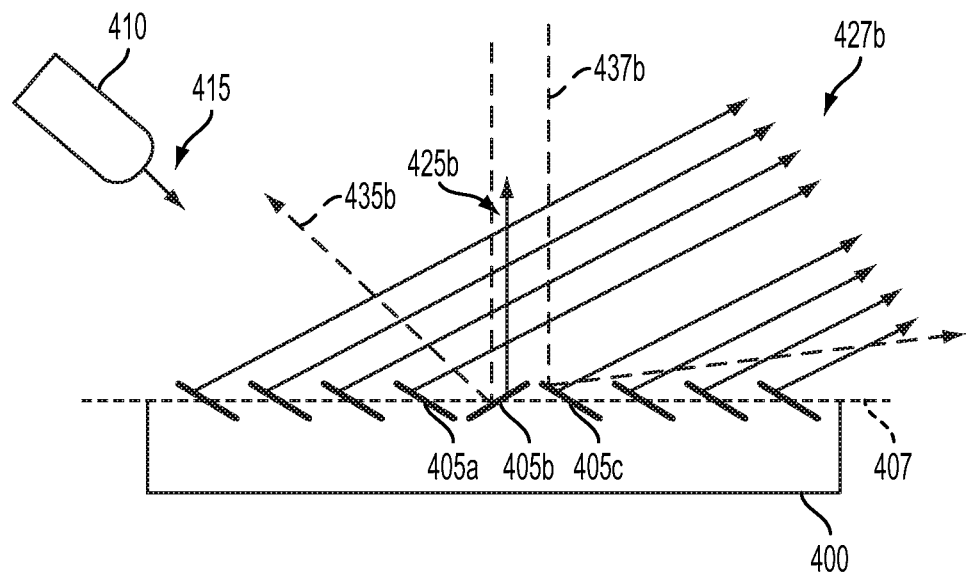
FIG. 4B illustrates a cross-section view of the elements of the example micromirror device of FIG. 4A reflecting laser light during a second period of time.

In some examples, an imaging system could include a micromirror device (MD) comprising a plurality of micromirrors disposed in a planar array (e.g., on a substantially flat surface of the MD). FIGS. 4A and 4B illustrate, in cross-section, such an MD 400. The MD 400 includes a plurality of micromirrors (e.g., 405a, 405b, 405c) disposed on a focal surface 407 of the MD 400. The MD 150 illustrated in FIG. 1 could be an MD similar to the MD 400 of FIGS. 4A and 4B. Each micromirror of the MD 400 is actuatable in that each micromirror has an angle that is electronically controllable. In some examples, this could include the individual micromirrors being configured to have one of two specified angles relative to the focal surface 407 (e.g., a first angle of positive 12 degrees relative to the plane of the focal surface 407 and a second angle of negative 12 degrees relative to the plane of the focal surface 407). Elements of an optical system (not shown, e.g., an objective, a relay lens system) could be configured to reflect and/or refract light from the MD 400 to a target (not shown) such that light emitted from the focal surface 407 (e.g., first illumination 415 emitted by a light source 410 and reflected from a particular mirror, e.g., 405b) is transmitted, in-focus, to corresponding locations on a focal surface on or within the target (e.g., a particular region within the target corresponding to the location of the particular mirror, e.g., 405b, on the focal surface 407).

FIG. 4A illustrates the operation of the MD 400 during a first period of time to actuate all of the micromirrors of the MD 400 to reflect first illumination 415 emitted from the light source 410 toward a target (not shown) as bright field illumination 425a. FIG. 4B illustrates the operation of the MD 400 during a second period of time to actuate a particular mirror 405b of the MD to have a first angle and to reflect first illumination 415 emitted from the light source 410 toward a particular region of the target (not shown) corresponding to the location of the particular mirror 405b on the focal surface 407 as confocal illumination 425. The remainder of the micromirrors of the MD 400 (e.g., 405a, 405b) are actuated to have a second angle and to reflect first illumination 415 emitted from the light source 410 as waste illumination 427b in a direction that is not toward the target (e.g., toward an optical sink or other heat sink element of an imager configured to dissipate the energy of the waste illumination 427b). The particular mirror 405b, actuated to the first angle, could also reflect conjugate light 435b from the particular region of the target toward an SLM, camera, or other elements of an imager (e.g., via an optical system configured to present such light, in-focus, to light-sensitive elements disposed on a focal plane of a camera). Other mirrors of the MD 400 (e.g., 405a, 405c), actuated to the second angle, could reflect non-conjugate light 437b from the target (e.g., from the particular region of the target, from other regions of the target illumination by the confocal illumination 425, from regions of the target illuminated by illumination scattered from such illumination portions of the target) toward an SLM, camera, or other elements of an imager (e.g., via an optical system configured to present such light, in-focus, to light-sensitive elements disposed on a focal plane of a camera).

Generally, an optical system of an imager (e.g., 100, an imager including one or more instances of an SLM, e.g., 110, 200, and/or an MD, e.g., 150, 400) that is configured to image a target and to determine spectrographic information for one or more regions of the target (e.g., to hyperspectrally image the target) could deliver light (e.g., illumination, image light) between elements of the imager (e.g., cameras, MDs, SLMs, apertures) and/or to and from a target in-focus. That is, such an optical system could define a number of focal surfaces of elements of the imager (e.g., a focal surface of an MD on which micromirrors of the MD are disposed, a focal surface of a camera on which light-sensitive elements (e.g., pixels) of the camera are disposed) that are conjugate to each other and/or to a focal surface on or within a target of the imaging system (e.g., as illustrated in FIG. 1). Related to such a configuration, locations on a particular focal surface (e.g., a particular region on a focal surface on or within a target) could correspond to locations on any focal surfaces conjugate to the particular focal surface (e.g., particular locations and/or micromirrors of an MD, particular locations and/or light-sensitive elements of a camera). The optical system could deliver light emitted from such locations in-focus to corresponding locations on the conjugate focal surface(s).

Figure 5B:
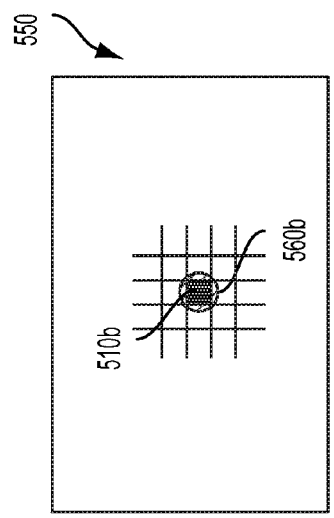
FIG. 5B illustrates an example focal surface of a camera illuminated by light reflected from the micromirror device of FIG. 5A.
Figure 5D:
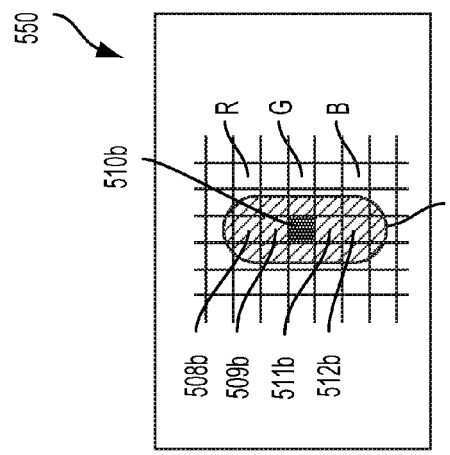
FIG. 5D illustrates an example focal surface of a camera illuminated by light reflected from the micromirror device of FIG. 5A.
Figure 5A:
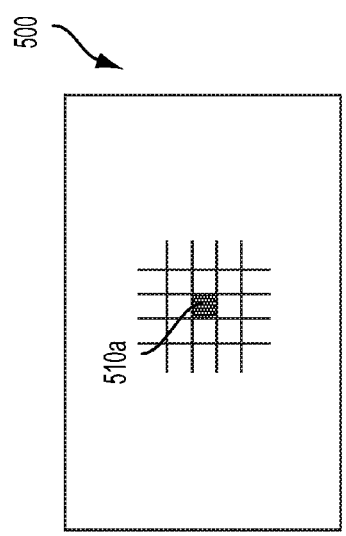
FIG. 5A illustrates an example configuration of a micromirror device.

As an illustrative example, FIG. 5A shows a configuration of an MD 500 comprising a square array of actuatable micromirrors wherein a single particular mirror 510a is operated to have a first angle and the remainder of the micromirrors are operated to have a second angle. The micromirrors of the MD are disposed on a focal surface of the MD and included in an imaging system that includes an optical system as described elsewhere herein. The optical system is configured to deliver illuminating light in-focus from micromirrors of the MD that are operated to have the first angle to corresponding locations on a focal surface on or within a target (i.e., locations on the focal surface on or within the target that correspond to the locations of the micromirrors on the focal surface of the MD). The optical system is further configured to direct light emitted from locations on the focal surface on or within the target in-focus to the focal surface of the MD, and further to direct light reflected from the MD by micromirrors actuated to the first angle in-focus to a focal plane of a camera (e.g., a focal plane on which a plurality of light-sensitive elements of the camera are disposed).

FIG. 5B illustrates the plurality of light-sensitive elements of such a camera 550b, including a particular light-sensitive element 510b located at a location on the focal surface of the camera corresponding to the location of the particular mirror 510a on the focal surface of the MD 500. As illustrated in FIG. 5B, light directed, by the optical system, from the MD 500 to the camera 550 is not reflected, refracted, or otherwise affected by an SLM or other chromatically dispersive elements as described herein, or is exposed to such an element that is being operated in a substantially non-dispersive mode (e.g., a refractive layer of such an SLM is being operated to have a substantially constant refractive index across the SLM). Such light, emitted from a particular region of the target located at a location on the focal surface on or within the target, reflected from the particular mirror 510a, and directed in-focus to the camera 500b, is illustrated as a spot of illumination 560b having a location corresponding to the location of the particular light-sensitive element 510b. The amplitude or other properties of the spot of illumination 560b could be detected by the particular light-sensitive element 510b and/or neighboring light-sensitive elements of the camera 550 to, e.g., determine an overall absorbance, emittance, reflectance, or other optical property of and/or otherwise image the particular region of the target.

Note that the presence of a single light-sensitive element 510b of the camera 550 in FIGS. 5B-E corresponding to a single mirror 510a of the MD 500 in FIG. 5A is meant as an illustrative example. A camera and corresponding MD of an imaging system could have the same resolution of light-sensitive elements and micromirrors, respectively (as shown in FIGS. 5A-E), or could have different resolutions. For example, a camera could include a plurality of light-sensitive elements disposed at a location on a focal surface of the camera corresponding to a single micromirror disposed at a corresponding location on a focal surface of the MD; that is, the camera could have a higher resolution that the MD. Other configurations of MDs, camera, optical systems, and other elements of an imager and other correspondences between light-sensitive element(s) of cameras, mirror(s) of micromirror devices, regions on a focal surface on or within a target, and other elements of an imager are anticipated. In some examples, a correspondence between light-sensitive elements of a camera, micromirrors of an MD, and/or regions of a target could be described by a model and/or calibration data (e.g., one or more point-spread functions) that could be determined by imaging a calibration target (e.g., a target having known specified spectrographic properties and/or spatial patterns thereof) or by some other method.

Figure 5C:
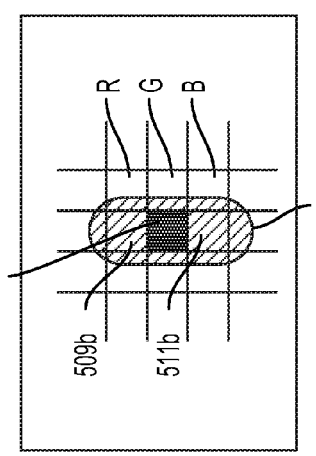
FIG. 5C illustrates an example focal surface of a camera illuminated by light reflected from the micromirror device of FIG. 5A.

FIG. 5C illustrates the plurality of light-sensitive elements of the camera 550 when light is directed, by the optical system, from the MD 500 to the camera 550 by being reflected, refracted, or otherwise affected by an SLM or other chromatically dispersive element (e.g., a prism or diffraction grating) to spectrally disperse the reflected light. Such light, emitted from a particular region of the target located at a location on the focal surface on or within the target, reflected from the particular mirror 510a, and directed in-focus to the camera 500, is illustrated as a band of spectrally disperse illumination 560c (the wavelength of light within the spectrally disperse illumination 560c being indicated by the a', 'G', and 'B' indicating red, green, and blue light, respectively) having a location corresponding to the location of the particular light-sensitive element 510b. The amplitude or other properties of the band of illumination 560c at various points within the band of illumination 560c (e.g., corresponding to second 509b and third 511b light-sensitive elements) could be detected by the particular light-sensitive element 510b and/or neighboring light-sensitive elements, e.g., 509b, 511b, of the camera 550 to, e.g., determine an absorbance, emittance, reflectance, or other optical property of the particular region of the target at respective corresponding wavelengths and/or ranges of wavelengths. For example, a degree of emission of green, red, and blue light by the particular region of the target in response to illumination could be detected by detecting an intensity of light received by the particular light-sensitive element 510b, the second light-sensitive element 509b, and the third light-sensitive element 511b, respectively.

A spectral resolution of such a system could be increased by increasing an amount of spectral dispersion of the light received by the camera 550 (e.g., by increasing a magnitude of a controlled gradient in the refractive index of a refractive layer or other element of an SLM operated and/or configured to spectrally disperse the light). FIG. 5D illustrates the plurality of light-sensitive elements of the camera 550 when light is directed, by the optical system, from the MD 500 to the camera 550 by being reflected, refracted, or otherwise affected by an SLM or other chromatically dispersive element(s) as described herein to spectrally disperse the reflected light to a greater degree than the degree of spectral dispersion illustrated in FIG. 5C. As a result, the band of spectrally disperse illumination 560*d* (the wavelength of light within the spectrally disperse illumination 560*d* being indicated by the 'R', 'G', and 'B' indicating red, green, and blue light, respectively) is longer and illuminates more light-sensitive elements of the camera 550. The amplitude or other properties of the band of illumination 560*d* at various points within the band of illumination 560*d* (e.g., corresponding to second 509*b*, third 511*b*, fourth 508*b*, and fifth 512*b* light-sensitive elements) could be detected by the particular light-sensitive element 510*b* and/or neighboring light-sensitive elements, e.g., 508*b*, 509*b*, 511*b*, 512*b*, of the camera 550 to, e.g., determine an absorbance, emittance, reflectance, or other optical property of the particular region of the target at respective corresponding wavelengths and/or ranges of wavelengths. Due to the increased spectral dispersion of the band of spectrally disperse illumination 560*d* relative to that illustrated in FIG. 5C, individual light-sensitive elements receive light from a narrower band of wavelengths relative to the scenario illustrated in FIG. 5C, resulting in a higher spectral resolution of spectrographic information determined from the operation of the camera.

Note that the spectral dispersion of light directed to light-sensitive elements of a camera need not be linear (e.g., as illustrated in FIGS. 5C and 5D). That is, bands of wavelengths of light received by neighboring light-sensitive elements could have different widths, e.g., a first light-sensitive element of a camera could receive light from a particular region of a target that has wavelengths between 550 nm and 560 nm while a neighboring light-sensitive element could receive light from the particular region of the target that has wavelengths between 560 nm and 590 nm. Such a correspondence between light-sensitive elements of a camera and corresponding regions of a target and ranges of wavelengths of light emitted from the target could be related to the operation of an SLM or other chromatically dispersive element (e.g., to a magnitude and/or gradient of a pattern of refractive index across a refractive later of an SLM). In some examples, a correspondence between light-sensitive elements of a camera and regions of a target and ranges of wavelengths of light emitted from the target could be described by a model and/or calibration data (e.g., one or more point-spread functions) that could be determined by imaging a calibration target (e.g., a target having known specified spectrographic properties and/or spatial patterns thereof) when an SLM is operated according to one or more patterns of refractive index or by some other method.

Note further that an overall pattern and/or level of spectral dispersion (e.g., a maximum possible level of change in wavelength of light received from a particular region of a target between adjacent light-sensitive elements) could depend, in addition to the configuration of an SLM and, e.g., the pattern of refractive index of a refractive layer of the SLM, on the configuration of the optical system to direct light to the SLM (e.g., from an MD, from a target, from an aperture) and to direct light from the SLM to the camera. For example, in the system 100 illustrated in FIG. 1, an amount of dispersion of the dispersed light 133 (e.g., a separation of light at two different wavelengths received from a particular region of the target 105 when focused on the foal surface 137 of the camera 130) could be related to a focal length of the relay lenses 143, 144. For example, configuring the relay lenses 143, 144 to have longer focal lengths could, for a given configuration and/or operation of the SLM 110, increase an amount of spectral dispersion in the dispersed light 133. Further, a level of collimation (e.g., a degree of planarity of the light collimated by the relay lens 143) of light presented to an SLM (e.g., 110) or other chromatically dispersive element could affect a pattern, linearity, uniformity (e.g., uniformity of degree and/or linearity of dispersion of light received from different locations of a target, e.g., 105, and/or MD, e.g., 150) or other properties of light spectrally dispersed by such an SLM or other chromatically dispersive element.

FIGS. 5A-5D illustrate the operation of an imaging system including an MD 500 to illuminate and to receive light from (i.e., to image) a single region of a target (e.g., a region having a location on a focal surface on or within the target corresponding to the location of the single particular mirror 510*a* that is controlled to have the first angle. A plurality of such regions could be sequentially imaged (e.g., a plurality of regions corresponding to the plurality of mirrors of the MD 500) by sequentially operating individual mirrors to illuminate such regions and to reflect light from such regions to a camera or other elements of an imager. However, a set of such mirrors could be controlled to have the first angle, such that a plurality of corresponding regions on the focal surface on or within the target could be simultaneously illuminated and/or imaged. The spacing of such regions and/or mirrors in such a set of mirrors on a focal surface of the MD could be specified to be greater than some minimum distance related to properties of the imager according to some application, e.g., to minimize out-of-focus light from illuminated regions of the target from being reflected by a mirror of the MD that does not correspond to such illuminated regions of the target. Additionally or alternatively, some other pattern of operation of mirrors of an MD (e.g., a pseudo-random pattern, a coded aperture, some other specified pattern(s)) could be used to illuminate, receive light from, or otherwise image or interact with regions of a tissue.

Figure 6A:
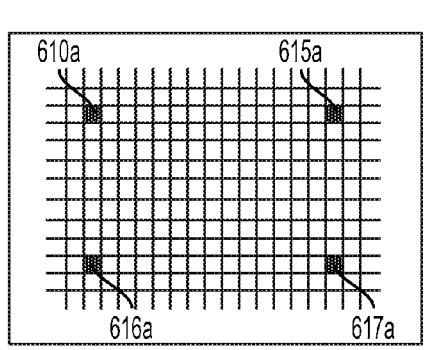
FIG. 6A illustrates a first configuration of an example micromirror device.

As an illustrative example, FIG. 6A shows a configuration of an MD 600 comprising a square array of actuatable micromirrors wherein a first set of particular mirrors 610*a*, 615*a*, 616*a*, 617*a* are operated to have a first angle and the remainder of the micromirrors are operated to have a second angle. The micromirrors of the MD are disposed on a focal surface of the MD and included in an imaging system that includes an optical system as described elsewhere herein. The optical system is configured to deliver illuminating light in-focus from micromirrors of the MD that are operated to have the first angle to corresponding locations on a focal surface on or within a target (i.e., locations on the focal surface on or within the target that correspond to the locations of the micromirrors 610*a*, 615*a*, 616*a*, and 617*a* on the focal surface of the MD when such mirrors are actuated to have the first angle). The optical system is further configured to direct light emitted from locations on the focal surface on or within the target in-focus to the focal surface of the MD, and further to direct light reflected from the MD by micromirrors actuated to the first angle in-focus to a focal plane of a camera (e.g., a focal plane on which a plurality of light-sensitive elements of the camera are disposed). Further, the optical system is configured to direct such received light from the MD 600 to the camera 650 by being reflected, refracted, or otherwise affected by an SLM or other chromatically dispersive element(s) as described herein to spectrally disperse the reflected light.

Figure 6B:
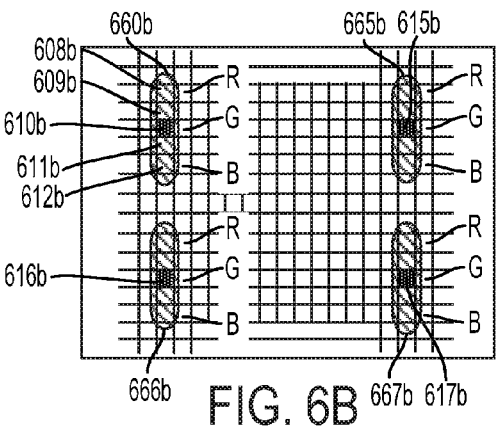
FIG. 6B illustrates an example focal surface of a camera illuminated by light reflected from the micromirror device of FIG. 6A.

FIG. 6B illustrates the plurality of light-sensitive elements of the camera 650 when light is directed, by the optical system, from particular regions of the target located at a locations on the focal surface on or within the target, reflected from the particular mirrors 610*a*, 615*a*, 616*a*, 617*a*, and directed in-focus to the camera 650. Such spectrally dispersed light received by the camera 650 is illustrated as bands of spectrally disperse illumination 660*b*, 665*b*, 666*b*, 667*b* (the wavelength of light within the spectrally disperse illumination being indicated by the 'R', 'G', and 'B' indicating red, green, and blue light, respectively) having respective locations corresponding to the locations of respective particular light-sensitive elements 610b, 615b, 616b, 617b. The amplitude or other properties of the bands of illumination 660b, 665b, 666b, 667b at various points within the bands of illumination 660b, 665b, 666b, 667b (e.g., corresponding to fifth 608b, sixth 609b, seventh 611b, and eighth 612b light-sensitive elements) could be detected by the particular light-sensitive elements 610b, 615b, 616b, 617b and/or neighboring light-sensitive elements, e.g., 608b, 609b, 611b, 612b, of the camera 650 to, e.g., determine an absorbance, emittance, reflectance, or other optical property of the particular regions of the target at respective corresponding wavelengths and/or ranges of wavelengths. For example, a degree of emission of green, red, orange-yellow, indigo, and blue light by the first particular region of the target 610a in response to illumination could be detected by detecting an intensity of light received by the particular light-sensitive element 610b, the fifth light-sensitive element 608b, the sixth light-sensitive element 609b, the seventh light-sensitive element 611b, and the eighth light-sensitive element 612b, respectively.

A speed of acquisition of images of the target by such a system could be increased by increasing the number of regions of the target that are imaged simultaneously by the imager (e.g., by increasing the number of mirrors of the MD that are controlled to have the first angle simultaneously). Correspondingly, a degree of spectral dispersion of the light received by the camera 650 and/or a spectral resolution of spectrographic information detected/determined for each of the regions could be reduced, e.g., to prevent overlap of light received from different regions of the target as projected onto light-sensitive elements of the camera 650. As an illustrative example, FIG. 6C shows a configuration of the MD 600 wherein a second set of particular mirrors (e.g., 610a, 613a, 616a, 618a) that are greater in number reduced in spacing across the surface of the MD 600 are operated to have the first angle and the remainder of the micromirrors are operated to have the second angle.

Figure 6C:
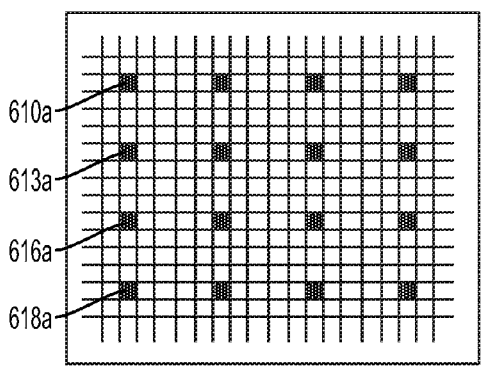
FIG. 6C illustrates a second configuration of the micromirror device of FIG. 6A.
Figure 6D:
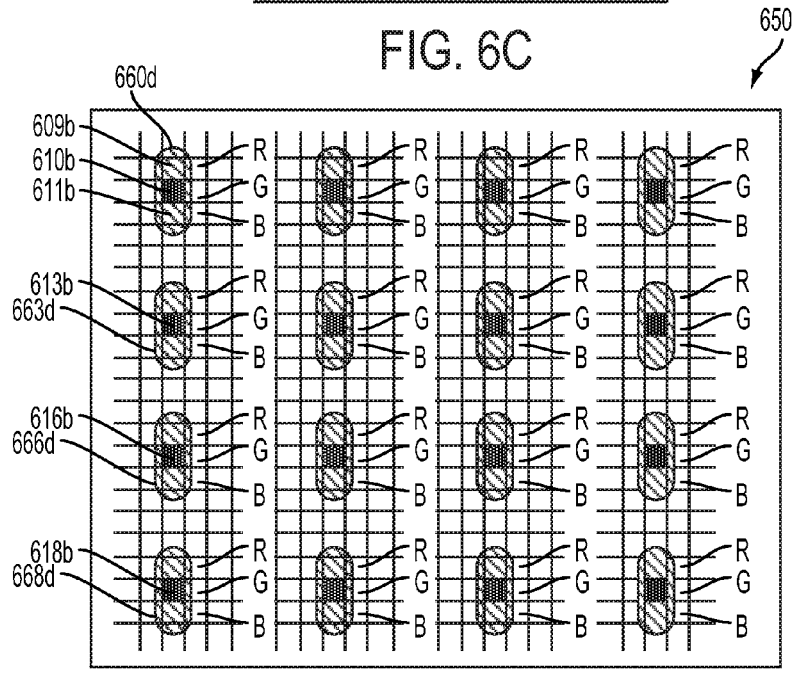
FIG. 6D illustrates an example focal surface of a camera illuminated by light reflected from the micromirror device of FIG. 6C.

FIG. 6D illustrates the plurality of light-sensitive elements of the camera 650 when light is directed, by the optical system, from the MD 600 (operated as shown in FIG. 6C) to the camera 650 by being reflected, refracted, or otherwise affected by an SLM or other chromatically dispersive element(s) as described herein to spectrally disperse the reflected light to a lesser degree than the degree of spectral dispersion illustrated in FIG. 6B. As a result, the bands of spectrally disperse illumination (e.g., 660d, 663d, 666d, 668d) corresponding to illuminated regions of the target and/or particular mirrors (e.g., 610a, 613a, 616a, 618a, respectively) of the second set of mirrors are longer and individually illuminate fewer light-sensitive elements of the camera 650. For example, the amplitude or other properties of a particular band of illumination 660d at various points within the band of illumination (e.g., corresponding to sixth 609b and seventh 611b light-sensitive elements) could be detected by the particular light-sensitive element 610b and/or neighboring light-sensitive elements, e.g., 609b, 611b, of the camera 650 to, e.g., determine an absorbance, emittance, reflectance, or other optical property of the corresponding particular region of the target at respective corresponding wavelengths and/or ranges of wavelengths. Due to the decreased spectral dispersion of the band of spectrally disperse illumination 660d relative to that illustrated in FIG. 6B (i.e., 660b), individual light-sensitive elements receive light from a wider band of wavelengths relative to the scenario illustrated in FIG. 6B, resulting in a lower spectral resolution of spectrographic information determined from the operation of the camera 650. Note that the example patterns of mirror operation shown in FIGS. 6A and 6D could be scanned sequentially across the MD 600 to allow imaging of an entire area of a target, or according to some other application.

In some examples, mirrors of an MD of an imaging system are actuatable to have one of two discrete angles (or some other discrete, finite number of angular or other states) relative to the MD (e.g., relative to the plane of a focal surface of the MD) such that an illumination light is reflected toward regions of the target corresponding to a first set of mirrors actuated to have a first angle. Such an imaging system could be further configured such that light responsively emitted from the corresponding regions of the target (i.e., conjugate light) is reflected in a first direction by mirrors of the first set and such that light responsively emitted from the non-corresponding regions (e.g., regions of the target illuminated by out-of-focus light, regions of the target illuminated by light scattered from the corresponding regions) of the target (i.e., non-conjugate light) is reflected in a second direction by a second set of mirrors actuated to have a second angle. In such examples, both the conjugate and the non-conjugate light could be used to image the target, to determine spectrographic information for regions of the target, or to determine some other information about the target.

Figure 7A:
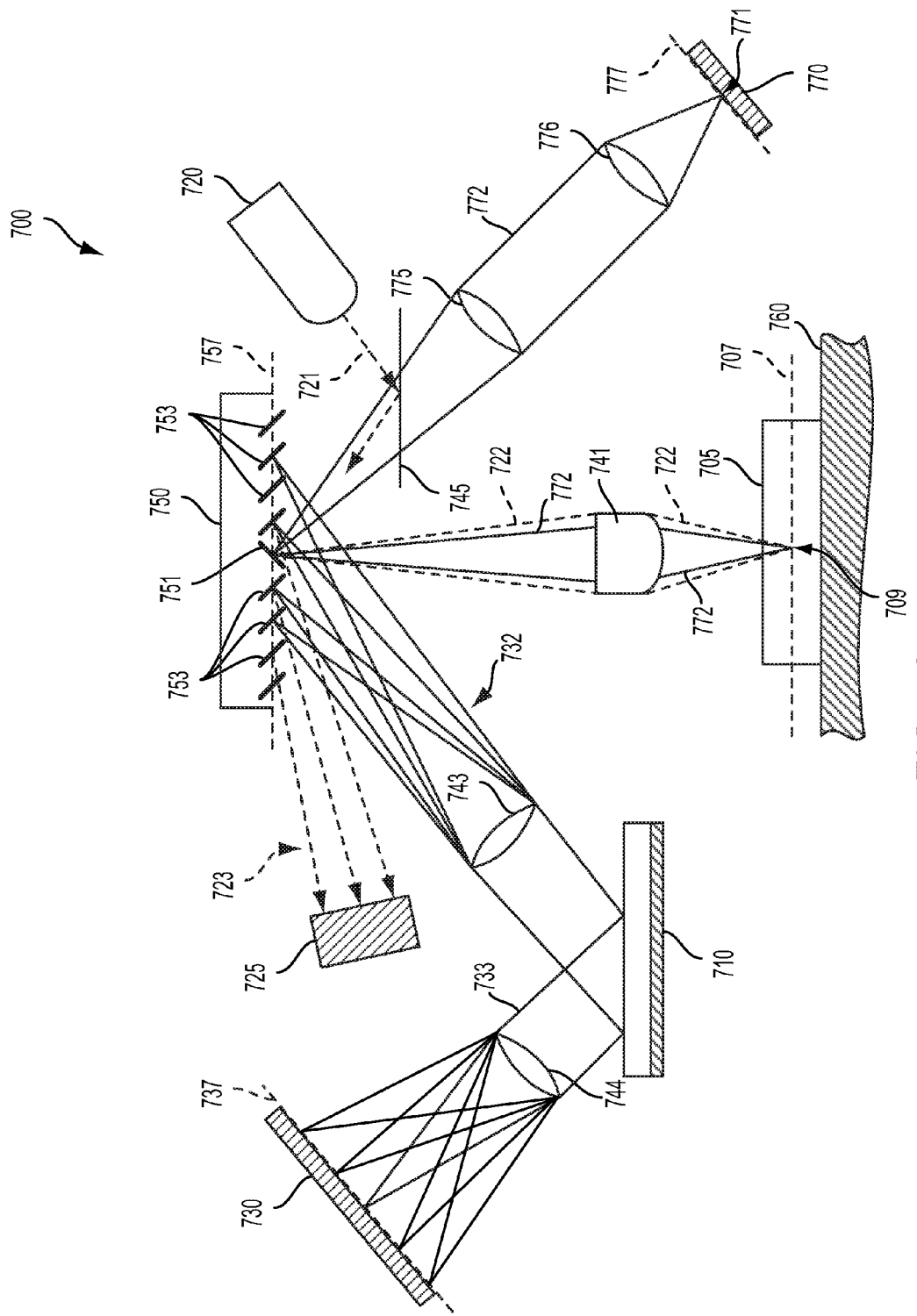
FIG. 7A illustrates an example imaging apparatus.

FIG. 7A illustrates in cross-section elements of an example imaging system 700 configured to image a target 705. The system 700 includes a light source 720 (e.g., a laser), a first camera 730 (illustrated as a plane of light-sensitive elements located on a focal plane 737 of the first camera 730), a second camera 770 (illustrated as a plane of light-sensitive elements located on a focal plane 777 of the first camera 770), a micromirror device (MD) 750, a spatial light modulator (SLM) 710, and an optical system (including an objective 741, first 743, second 744, third 775, and fourth 776 relay lenses, a dichroic mirror 745, and an optical sink 725) configured to direct light to and from the target 705 and between the elements of the system 700. The system 700 additionally includes a stage 760 to which the target 705 is mounted. Note that the MD 750 and first 730 and second 770 cameras comprise two-dimensional arrays of micromirrors and light-sensitive elements, respectively. Further, note that the optical system (e.g., 741, 743, 744, 745, 775, 776) and SLM 710 are configured to direct light between the target 705, MD 550, and first 730 and second 770 cameras such that locations on the focal surfaces 757, 737, 777 of the MD 750 and cameras 730, 770 correspond to respective locations on the focal surface 707 in the target 705.

The system 700 illuminates a specified region 709 on a focal surface 707 in the target 705 by emitting a first illumination 721 from the light source 720 and reflecting the first illumination 721 from the dichroic mirror 745 toward the MD 750. A selected mirror 751 of the MD 750 that has a location on a focal surface 757 of the MD 750 corresponding to the specified region 709 is controlled to have a first angle to reflect the first illumination 721 toward the target 705 as confocal illumination 722 via the objective 741. Other mirrors 753 of the MD 750 are controlled to have a second angle to reflect the remainder of the first illumination 721 as waste illumination 723 toward the optical sink 725 to be absorbed. As illustrated, a single mirror (751) is controlled to illuminate (and to receive light from) a corresponding region 709 of the target 705; however, additional mirrors (e.g., selected from other mirrors 753) could be operated simultaneously, sequentially, or according to some other scheme to illuminate (and to receive light from) corresponding additional regions of the target 705.

The system 700 receives light (including conjugate light 772) emitted from the target 705 (e.g., from the specified region 709) in response to illumination via the objective 741. The conjugate light 772 is directed, in-focus, to a specified region 771 on a focal surface 777 of the second camera 770 corresponding to the specified region 709 (e.g., to a region of the second camera having one or more light-sensitive elements and/or pixels of the second camera 770). Such light is directed to the second camera 770 from the MD 750 via relay optics 775, 776 or via some other optical element(s).

The system 700 also receives non-conjugate light 732 emitted from the target (e.g., from regions of the target illuminated out-of-focus by the confocal illumination 722, from regions of the target illuminated by light scattered from such regions and/or scattered from the specified region 709) via the objective 741. The non-conjugate light 732 arrives, in-focus, at the focal surface 757 of the MD 750 and reflected by mirrors of the MD 750 that are controlled to have the second angle (e.g., 753) toward the SLM 710. The first relay lens 743 (and/or some other optical elements of the system 700) collimates the received light and presents the substantially collimated light to the SLM 710. The SLM 700 reflects the non-conjugate light 732 as spectrally dispersed light 733 toward the second relay lens 744 that is configured to present the spectrally dispersed light 733 in-focus to a focal surface 737 of the first camera 730. The SLM 710 is configured and/or operated such that the spectrally dispersed light 733 is spectrally dispersed relative to the non-conjugate light 732 in a controlled manner such that spectrographic information of one or more particular regions of the target 705 and/or of the non-conjugate light 732 can be detected or determined (e.g., based on a plurality of images of the target 705 generated by the first camera 730 during respective periods of time when the SLM 710 is operated according to a respective plurality of patterns of refractive index, e.g., a plurality of controlled gradients having respective different magnitudes and/or directions). In some examples, the spectrally dispersed light 733 is spectrally dispersed in a manner related to an electronically controlled direction, magnitude, and/or some other property of a spatial gradient in the refractive index of a layer of the SLM 710.

Note that the configuration and/or operation of the system 700 to illuminate and to receive conjugate light from a specified region 709 on a focal surface 707 of the target 705 is intended as a non-limiting example. Alternatively, a larger and/or differently-shaped region of the target (e.g., a line within the target; substantially the entire target and/or the entire target within a field of view of the imaging system 700) could be illuminated by operating the mirrors 751, 753 of the MD 750 according to a different set of controlled angles than those illustrated. For example, a plurality of spatially separated regions proximate to the focal surface 707 of the target 705 could be illuminated and imaged simultaneously by controlling a corresponding plurality of spatially separated mirrors of the MD 750 to reflect the first illumination 721 toward the plurality of the regions of the target 705. The mirrors 751, 753 of the MD 750 could be controlled according to some other pattern, e.g., to approximate some other coded aperture on the focal surface 757 of the MD 750. Further, the light source 720 could emit illumination at a controllable wavelength (e.g., illumination that is substantially monochromatic, but having a wavelength that can be altered by operation of the light source) and spectrographic information could be determined for regions of the target 705 based on images of the target 705 generated when the target 705 is illuminated by different wavelengths of light (e.g., to generate a corresponding plurality of emission spectra for the region corresponding to the different wavelengths of illumination).

The system 700 could be operated in a variety of ways to provide confocal, hyperspectral, or other types of images of the target 705. For example, the system could be operated during a number of specified periods of time to illuminate regions of the target (e.g., by controlling respective specified sets of mirrors of the DM to have first or second angles), to electronically control a gradient of refractive index across a refractive layer of the SLM to have respective different specified magnitude(s) or direction(s) or to control the refractive index of element(s) of the SLM according to some other patterns, to image conjugate or non-conjugate light received from the target 705 using the second 770 and first 730 cameras, respectively, or to operate some other element(s) of the system 700 over time according to an application.

Figure 7B:
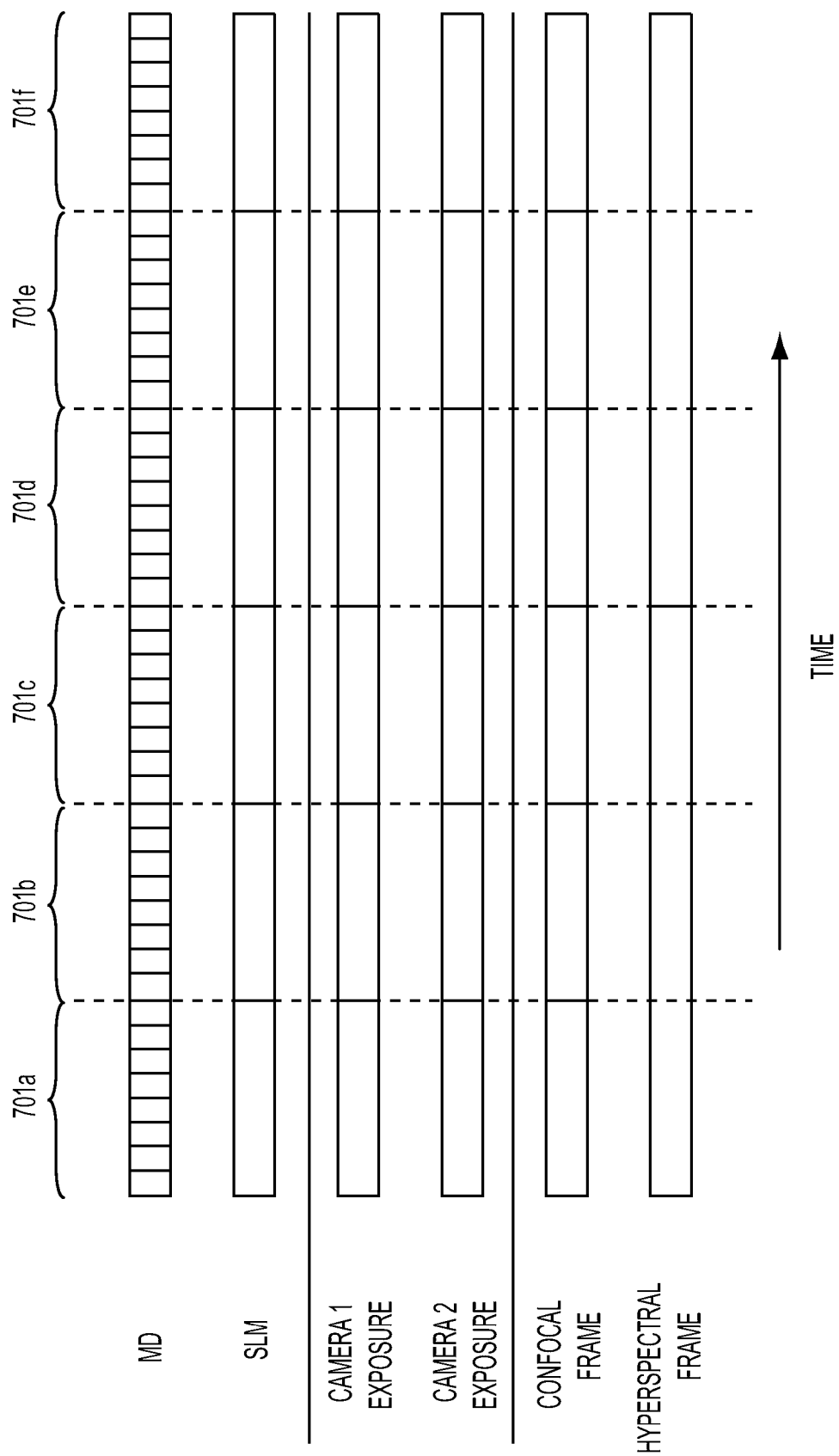
FIG. 7B illustrates an example timing diagram for operation of elements of the imaging apparatus of FIG. 7A.

FIG. 7B is a timing diagram illustrating an example operation of the system 700 to generate monochromatic confocal images of the target 705 using the second camera 770 and to generate bright-field hyperspectral images of the target 705 using the first camera 730. Each horizontal trace indicates, by enclosed boxes, the timing of operation of various elements of the system 700 according to respective different configurations. Each box of the 'MD' trace indicates a period of time during which the mirrors of the MD 750 are controlled according to a specified pattern; for example, each box could represent the operation of respective disjoint sets of mirrors of the MD 750 to illuminate respective different regions of the target 705 in a scanning fashion in order to illuminate, in turn, all regions of the target 705. Each box of the 'SLM' trace indicates a period of time during which the MD 710 is electronically controlled to have a respective pattern of refractive index across a refractive layer of the SLM; for example, each box could represent the operation of the SLM 710 to have a controlled gradient in a different direction (e.g., as illustrated in FIGS. 3B-D) to disperse light imaged by the first camera 730 in respective different directions. Each box of the 'CAMERA 1 EXPOSURE' and 'CAMERA 2 EXPOSURE' traces indicates a period of time during which the cameras 730, 770 are operated to generate respective images of light received by the cameras 730, 770; these periods of time could represent an exposure time or integration time of light-sensitive elements of the cameras 730, 770 (e.g., of a CCD array of the cameras, of an array of active pixel sensors of the cameras). Further, specified first 701a, second 701b, third 701c, fourth 701d, fifth 701e, and sixth 701f periods of time are indicated in FIG. 7B and correspond to exposure times for the first 730 and second 770 cameras.

When the system 700 is operated as shown, a number of confocal images and hyperspectral images of the target 705 could be generated based on images generated by the first 730 and/or second 770 cameras. If the various MD 750 settings used during a particular second camera 770 exposure (e.g., the exposure that occurs during the first period of time 701a) are specified to scan across the target (e.g., to sequentially illuminate and to receive light from respective regions of the target 705 such that, at some point in time during the exposure, all regions of the target 705 are illuminated), individual images generated by the second camera 770 could be used to generate respective confocal images of the target 705 (corresponding to periods of time indicated by the 'CONFOCAL FRAME' trace of FIG. 7B). This could include scaling or normalizing an image generated by the second camera 770 (e.g., according to calibration data describing the optical properties of the system 700) to generate a corresponding confocal image of the target 705.

When the system 700 is operated in such a manner, sets of multiple images generated by the first camera 730 (e.g., during the first 701a, second 701b, and third 701c periods of time) could be used to generate respective hyperspectral images of the target 705 (corresponding to periods of time indicated by the 'HYPERSPECTRAL FRAME' trace of FIG. 7B). Such a determination could include processes as described herein (e.g., a process of deconvolution, a process similar to the process described by example in relation to FIGS. 3A-D, some other process(es)). Such processes could be based on a description of correspondences between the location of light-sensitive elements of the first camera and corresponding locations on or within the target. Such correspondences could be wavelength-dependent and could be determined based on a model of the system 700 (e.g., based on the magnitude and direction of a gradient of refractive index of the refractive layer across the SLM 710 during one or more periods of time, e.g., 701a, 701b, 701c) and/or on an empirical measurement of the properties of the system 700 (e.g., based on a set of images of a calibration target having known spectrographic information/content or some other calibration information or procedure).

Note that the timing diagrams illustrated in FIG. 7B to describe the operation of elements of the system 700 are intended as a non-limiting example. Other timings of operation of the system 700 are anticipated. Further, spectrographic information, images, or other information about regions of the target 705 could be determined based on a combination of information (e.g., images) generated by the first 730 and second 770 cameras. The system 700 could be operated according to a variety of different operational modes. For example, in a first mode the system 700 could be operated only to generate confocal images of the target 705 and the SLM 710 and first camera 730 could be disabled. The system 700 could include a further light source or be otherwise configured such that the SLM 710 and first camera 730 could be operated, in combination with the further light source and MD 750, to image conjugate light received from the target 705 (e.g., similar to the configuration of system 100) while the second camera 770 could be operated to generate brightfield images of the target 705. Other configurations and operations of the system 700, or of other systems and embodiments as described herein (e.g., 100, 200, 400, 500) are anticipated.

The system 700 could be operated to provide a sequence of hyperspectral images at a specified temporal, spatial, and/or spectral resolution. In some examples, this could include reducing a first resolution to increase a second resolution. For example, a temporal resolution (e.g., a number of hyperspectral images produced per second) could be increased by increasing a number of regions of the target 705 simultaneously imaged (e.g., by increasing a number of spatially distinct mirrors of the MD 750 used to simultaneously illuminate respective spatially distinct regions of the target 705) such that the whole target could be imaged using fewer corresponding MD 750 configurations (i.e., patterns of controlled angles of mirrors of the MD 750). Correspondingly, a spectral resolution of the images could be reduced (e.g., by reducing a degree of spectral dispersion of received light caused by the SLM 710) to prevent overlap of light received from different regions of the target on light-sensitive elements of the first camera 730 (a similar scenario is described in relation to FIGS. 6A-D). In some examples, such resolutions (e.g., spatial, temporal, spectral) could be specified by a user. Additionally or alternatively, one or more such resolutions could be set automatically by a controller of the system 700 (e.g., to maximize spatial and/or temporal resolution while maintaining spectral resolution at a minimum level sufficient to distinguish emission peaks of respective different fluorophores in the target 705). Other configurations and operations of systems and methods described herein are anticipated.

IV. Example Electronics of an Imaging Apparatus

Figure 8:
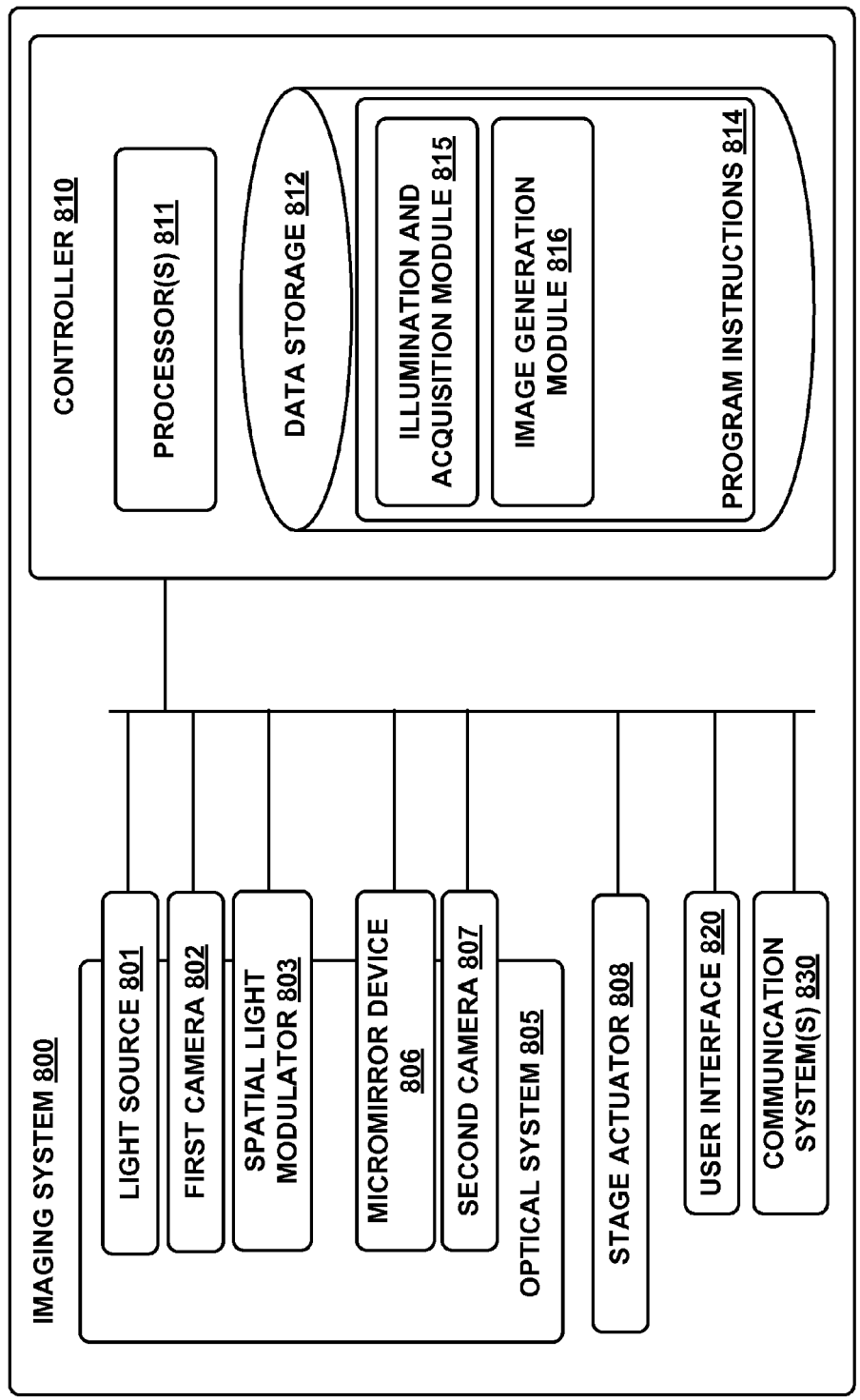
FIG. 8 is a functional block diagram of an example imaging system.

FIG. 8 is a simplified block diagram illustrating the components of an imaging system 800, according to an example embodiment. Imaging system 800 and/or elements thereof may take the form of or be similar to one of the example systems or elements 100, 200, 400, 700 shown in FIGS. 1, 2A, 4A-B, and 7A. Imaging system 800 may take a variety of forms, such as a wall, table, ceiling, or floor-mounted device. Imaging system 800 may take the form of a bench-top or table-top device (e.g., a bench-top microscope). Imaging system 800 and/or elements thereof could also take the form of a system, device, or combination of devices that is configured to be part of another device, apparatus, or system. For example, imaging system 800 or element(s) thereof (e.g., spatial light modulator 803) could take the form of a system or element configured to be mounted to or otherwise disposed as part of some other imaging system (e.g., imaging system 800 and/or the spatial light modulator 803 or other elements thereof could be configured to be part of a confocal microscope or other imaging system, e.g., to spectrally disperse one or more beams or fields of light of the imaging system in an electronically-controllable manner). Imaging system 800 could take the form of a system configured to contents of an industrial environment (e.g., to image integrated circuits, microelectromechanical devices, or other objects in a clean room), medical environment, scientific environment, or some other environment. Imaging system 800 also could take other forms.

In particular, FIG. 8 shows an example of an imaging system 800 having a light source 801, a first camera 802, a spatial light modulator (SLM) 803, a micromirror device (MD) 806, a second camera 807, an optical system 805, a stage actuator 808, a user interface 820, communication system(s) 830 for transmitting data to a remote system, and controller 810. The components of the imaging system 800 may be disposed on or within a mount or housing or on some other structure for mounting the system to enable stable imaging or other functions relative to a target of interest, for example, a biological sample mounted to a stage (e.g., a stage having a location relative to other elements of the imaging system 800 that is actuated in at least one dimension by the stage actuator 808). The imaging system 800 could include additional components, for example, a perfusion pump configured to provide aerated or otherwise chemically specified perfusate to a cell culture or other biological sample comprising a target of the imaging system 800, one or more electrophysiological or optogenetic stimulators and/or sensors, an integrated circuit test rig, or some other instrument(s) or other component(s) according to an application.

The light source 801, cameras 802, optical system 805, SLM 803, MD 806, and/or stage actuator 808 could be configured and/or disposed as part of the imaging device 800 as described elsewhere for similar elements. The optical system 805 is configured to direct light emitted by the light source 801 to illuminate one or more regions of a target (e.g., via reflection from one or more mirrors of the MD 806). The optical system 805 is further configured to receive light responsively emitted from the target and to direct such light and/or components of such light (e.g., a conjugate component of the received light, a non-conjugate component of the received light) to one or both of the cameras 801, 807 (e.g., via reflection from one or more mirrors of the MD 806, via reflection from, transmission through, or some other chromatically disperse interaction with the SLM 803). The optical system 805 is configured to direct such light between elements (e.g., 802, 806, 807) of the imaging system 800 such that focal surfaces of one or more such elements (e.g., a focal surface of the camera(s) 801, 807 on which is disposed light-sensitive elements of the camera(s), a focal surface of the MD 806 on which is disposed mirrors of the MD 806) are optically conjugate with each other and/or with a focal surface on or within a target of the imaging system 800.

Controller 810 may be provided as a computing device that includes one or more processors 811. The one or more processors 811 can be configured to execute computer-readable program instructions 814 that are stored in a computer readable data storage 812 and that are executable to provide the functionality of an imaging system 800 as described herein.

The computer readable data storage 812 may include or take the form of one or more non-transitory, computer-readable storage media that can be read or accessed by at least one processor 811. The one or more computer-readable storage media can include volatile and/or non-volatile storage components, such as optical, magnetic, organic or other memory or disc storage, which can be integrated in whole or in part with at least one of the one or more processors 811. In some embodiments, the computer readable data storage 812 can be implemented using a single physical device (e.g., one optical, magnetic, organic or other memory or disc storage unit), while in other embodiments, the computer readable data storage 812 can be implemented using two or more physical devices.

The program instructions 814 stored on the computer readable data storage 812 may include instructions to perform any of the methods described herein. For instance, in the illustrated embodiment, program instructions 814 include an illumination and acquisition module 815 and an image generation module 816.

The illumination and acquisition module 815 can include instructions for operating the light source 801, first camera 802, SLM 803, MD 806, second camera 807, and/or stage actuator 808 to enable any of the functions or applications of an imaging system to determine and/or detect spectrographic information about regions of a target and/or to hyperspectrally image, confocally image, or otherwise image or optically interact with a target as described herein. Generally, instructions in the illumination and acquisition module 815 describe methods of operating the light source 801 and/or MD 806 to illuminate one or more regions of a target with light at one or more specified wavelengths during one or more respective periods of time. Instructions in the illumination and acquisition module 815 further describe methods of operating the SLM 803 to spectrally disperse light directed toward the SLM 803 according to one or more specified directions, magnitudes, or other properties of dispersion of light during one or more respective periods of time (e.g., periods of time synchronous with and/or overlapping periods of time of operation of the MD 806 and/or light source 801).

Instructions in the illumination and acquisition module 815 further describe methods of operating the camera(s) 801, 807 to generate images of light received from illuminated regions of a target via the optical system 805, micromirror device 806, and/or SLM 803 during one or more periods of time (e.g., periods of time of operation of the MD 806, SLM 803, light source 801, or other components of the imaging system 800). In some examples, generating an image using the camera(s) 801, 807 could include reading out information (e.g., values or signals describing of related to the intensity or other property light detected by light-sensitive elements of the camera(s) 801, 807. In such examples, a particular light-sensitive element or set of light-sensitive elements of the camera could be substantially unable to detect light when being read out. For example, one or both of the camera(s) could be CMOS cameras configured to have a global shutter (i.e., to read out an entire frame of image data from the camera at a time) and/or to have a rolling shutter (i.e., to read out a row of image data from the camera at a time). In such embodiments, the illumination and acquisition module 815 could describe operations of an MD 806 or other elements to not illuminate regions of a target corresponding to locations (e.g., light-sensitive elements) of the camera(s) that are not able to detect light from such regions (e.g., light-sensitive elements that are being read out). For example, one of the camera(s) 801, 807 could comprise a CMOS camera configured or operated to have a global shutter, and the illumination and acquisition module 815 could describe operation of the imaging system 800 such that substantially no regions of the target are illuminated by the light source 801 when the CMOS camera is being read out. Other operations, functions, and applications of the light source 801, first camera 802, SLM 803, MD 806, second camera 807, stage actuator 808, and/or of other components of the imaging system 800 as described herein could be implemented as program instructions in the illumination and detection module 815.

The image generation module 816 can include instructions for generating one or more images of the target and/or determining some other information about the target (e.g., spectrographic information for one or more regions of the target, the identity of contents of a region of the target based on such determined spectrographic information) based on one or more images generated by the camera(s) 801, 807. For example, the image generation module 816 can include instructions for generating one or more images of the target (e.g., monochrome confocal images) by scaling or normalizing an image generated by one or both of the cameras 801, 807 (e.g., according to calibration data describing the optical properties of the system 800). The image generation module 816 can include instructions for generating spectrographic information about one or more regions of a target (e.g., to generate a hyperspectral image of the target) based on one or more images of spectrally dispersed light received from the target. Such a determination could include processes as described herein (e.g., a process of deconvolution, a process similar to the process described by example in relation to FIGS. 3A-D, some other process(es)). Such processes could be based on a description of correspondences between the location of light-sensitive elements of the camera(s) 801, 807 and corresponding locations on or within the target. Such correspondences could be wavelength-dependent and could be determined based on a model of the imaging system 800 (e.g., based on the magnitude and direction of a gradient of refractive index of a refractive layer across the SLM 803 during one or more periods of time corresponding to images generated by the camera(s) 801, 807) and/or on an empirical measurement of the properties of the system 800 (e.g., based on a set of images of a calibration target having known spectrographic information/content or some other calibration information or procedure).

Some of the program instructions of the illumination and acquisition module 815 and/or image generation module 816 may, in some examples, be stored in a computer-readable medium and executed by a processor located external to the imaging system 800. For example, the imaging system 800 could be configured to illuminate and to receive light from a target (e.g., a biological sample) and then transmit related data to a remote server, which may include a mobile device, a personal computer, the cloud, or any other remote system, for further processing (e.g., for the determination of spectrographic information of one or more regions of the target, for identifying the region of the target and/or contents thereof based on the determined spectrographic content, to generate a hyperspectral image or other variety of image of the target).

User interface 820 could include indicators, displays, buttons, touchscreens, head-mounted displays, and/or other elements configured to present information about the imaging system 800 to a user and/or to allow the user to operate the imaging system 800. Additionally or alternatively, the imaging system 800 could be configured to communicate with another system (e.g., a cellphone, a tablet, a computer, a remote server) and to present elements of a user interface using the remote system. The user interface 820 could be disposed proximate to the light source 801, first camera 802, SLM 803, MD 806, second camera 807, stage actuator 808, controller 810, or other elements of the imaging system 800 or could be disposed away from other elements of the imaging system 800 and could further be in wired or wireless communication with the other elements of the imaging system 800. The user interface 820 could be configured to allow a user to specify some operation, function, or property of operation of the imaging system 800. The user interface 820 could be configured to present an image (e.g., a hyperspectral image) of target generated by the imaging system 800 or to present some other information to a user. Other configurations and methods of operation of a user interface 820 are anticipated.

Communication system(s) 830 may also be operated by instructions within the program instructions 814, such as instructions for sending and/or receiving information via a wireless antenna, which may be disposed on or in the imaging system 800. The communication system(s) 830 can optionally include one or more oscillators, mixers, frequency injectors, etc. to modulate and/or demodulate information on a carrier frequency to be transmitted and/or received by the antenna. In some examples, the imaging system 800 is configured to indicate an output from the controller 810 (e.g., one or more images of a target) by transmitting an electromagnetic or other wireless signal according to one or more wireless communications standards (e.g., Bluetooth, WiFi, IRdA, ZigBee, WiMAX, LTE). In some examples, the communication system(s) 830 could include one or more wired communications interfaces and the imaging system 800 could be configured to indicate an output from the controller 810 by operating the one or more wired communications interfaces according to one or more wired communications standards (e.g., USB, FireWire, Ethernet, RS-232).

The computer readable data storage 812 may further contain other data or information, such as contain calibration data corresponding to a configuration of the imaging system 800, a calibration target, or some other information. Calibration, imaging, and/or other data may also be generated by a remote server and transmitted to the imaging system 800 via communication system(s) 830.

V. Example Methods

Figure 9:
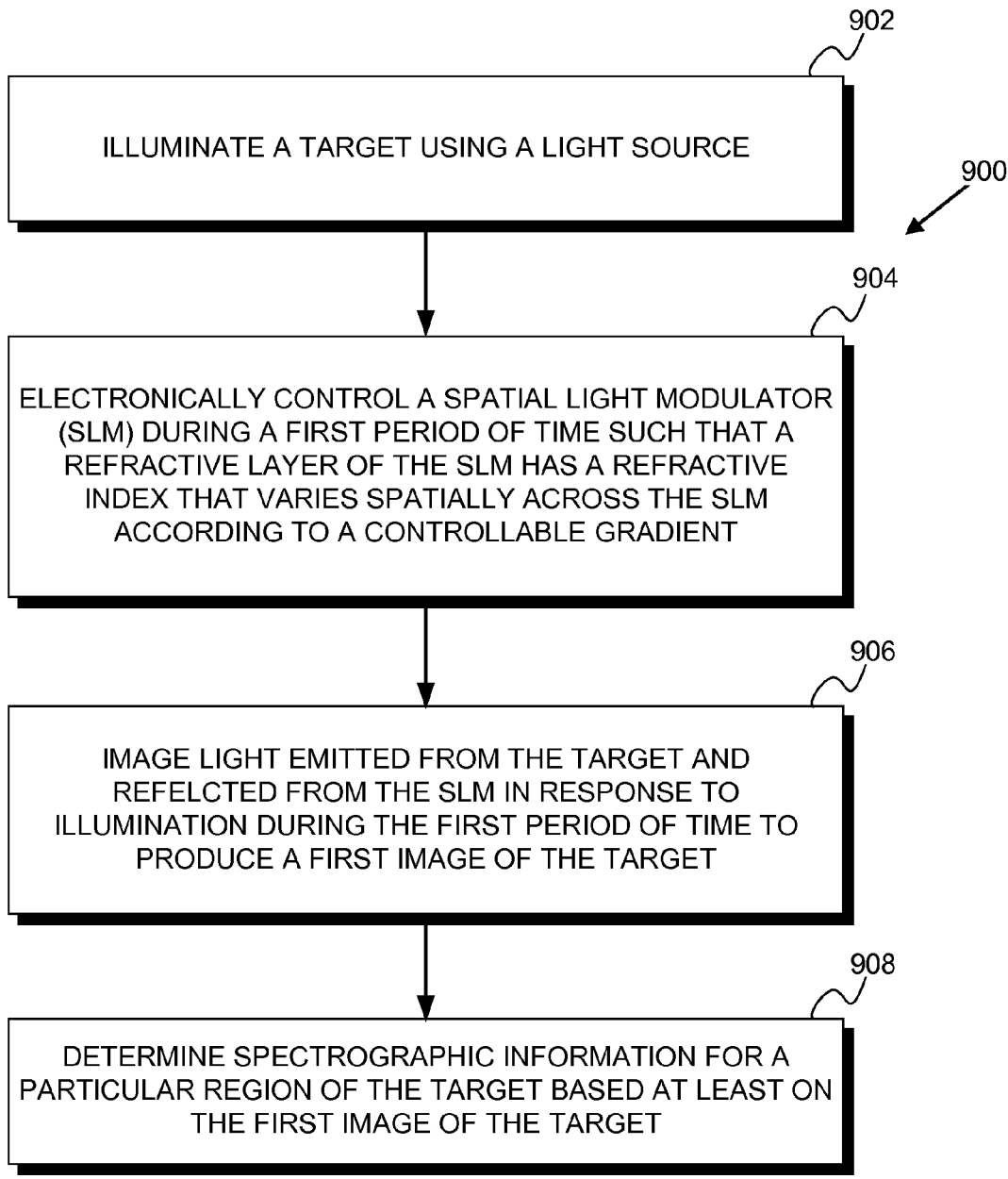
FIG. 9 is a flowchart of an example method.

FIG. 9 is a flowchart of an example method 900 for operating elements of an imaging system to perform functions and/or applications of the imaging system. The method 900 includes operating a light source to illuminate a target (902). This could include operating a light-emitting element (e.g., a laser) of the light source to illuminate the target and/or one or more regions thereof with light at a particular fixed wavelength (e.g., an excitation wavelength of one or more fluorophores in the target). This (902) could include illuminating one or more particular regions located on a focal surface on or within the target, e.g., by operating one or more mirrors of a micromirror device to reflect light from the light source to the one or more particular regions. Illuminating the target (902) could include illuminating the target according to some other pattern or method (e.g., according to a coded aperture, a pattern of structured illumination, or according to some other pattern(s)).

The method 900 additionally includes electronically controlling a spatial light modulator (SLM) during a first period of time such that a refractive index of the SLM has a refractive index that varies according to a controllable gradient (904). In some examples, the controlled refractive index could be a refractive index of a chromatically disperse refractive layer such that light directed toward, reflected from, transmitted through, or otherwise having interacted with the SLM is spectrally dispersed. In some examples, the SLM could further include a reflective layer disposed beneath the refractive layer. In some examples, the SLM could include an array of cells having respective electronically controllable refractive indexes and electronically controlling the SLM (904) could include electronically controlling the refractive indexes of the cells such that the refractive indexes of the cells vary in a direction corresponding to a specified direction of the controllable gradient at a spatial rate of change corresponding to a specified magnitude of the controllable gradient.

The method 900 additionally includes imaging light emitted from the target and reflected from the SLM in response to illumination during the first period of time to produce a first image of the target (906). This could include an optical system receiving the light emitted from the target and directing the received light (e.g., via reflection from one or more mirrors of a micromirror device) toward the SLM. This (906) could include the optical system collimating such received light before directing the collimated received light toward the SLM. This (906) could include the optical system directing such light in-focus to a focal surface of a camera or other element(s) configured to image the emitted light, i.e., the optical system could be configured such that a focal surface on or within the target is optically conjugate to a focal surface of a camera (e.g., a surface of the camera on which a plurality of light-sensitive elements of the camera are disposed). This (906) could include controlling a spectral resolution of spectrographic information determined using the method 900 by controlling a magnitude of the controllable gradient.

The method 900 additionally includes determining spectrographic information for a particular region of the target based at least on the first image of the target (908). Determining spectrographic information for the particular region (908) could include determining the intensity of a beam of light emitted from the particular region at different wavelengths based on corresponding different pixels of the first image of the target. In some examples, the method 900 could include imaging light emitted from the target and reflected from the SLM in response to illumination during a plurality of respective further periods of time when the SLM is operated to have respective different refractive index patterns (e.g., substantially linear gradients having respective directions and/or magnitudes). In such examples, determining spectrographic information for the particular region (908) could include determining such information based on the first image and the plurality of further images of the target, e.g., by a process of deconvolution.

The method 900 could further include determining calibration information for the imaging system. For example, a calibration target having one or more known patterns of spectrographic properties could be imaged. A correspondence between individual light-sensitive elements of a camera or other element(s) of a system used to image the calibration target and the location of a range of regions of the calibration target at a range of corresponding wavelengths could be determined and such a correspondence could be used to determine calibration information for the imaging system. Additionally or alternatively, such calibration information could be based on a model of operation of the imaging system (e.g., a model of the geometric and optical properties of the imaging system).

The method 900 could include other additional steps or elements. The method 900 could include any additional steps, or could include details of implementation of the listed steps 902, 904, 906, 908 or of other additional steps, as described herein in relation to the operation of an imaging system. Additional and alternative steps of the method 900 are anticipated.

VI. Conclusion

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to image biological environments (e.g., tissues extracted from a human body), it is noted that the disclosed devices, systems, and methods can be applied in other contexts as well. For example, imaging systems configured as disclosed herein may be included as part of other scientific and/or industrial imaging apparatus. In some contexts, such an imaging system could be operated to image an integrated circuit, a microelectromechanical device, or some other microfabricated device. In another example, an imaging system could be configured to image some other device or object. For example, the imaging system could be configured and/or applied to image a surface of an electrode, an implant, a bearing, a mineral sample, or some other device or object (e.g., to determine a surface geometry of an object, to determine a disposition of elements or chemical on or within a surface of an object).

Additionally, while various aspects and embodiments have been disclosed herein, other aspects and embodiments will be apparent to those skilled in the art. The various aspects and embodiments disclosed herein are included for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
a light source;
a first camera, wherein the first camera comprises a plurality of light-sensitive elements disposed on a focal surface of the first camera;
a spatial light modulator, wherein the spatial light modulator comprises a reflective layer disposed beneath a refractive layer, wherein the refractive layer is configured to have a refractive index that varies spatially across the spatial light modulator according to a controllable gradient, wherein at least the direction and magnitude of the controllable gradient are electronically controllable, and wherein the refractive layer is chromatically dispersive; and
an optical system, wherein the optical system is configured to (i) direct light from the light source to a target, (ii) direct light emitted from the target in response to the light from the light source toward the spatial light modulator, and (iii) direct light emitted from the target and reflected from the spatial light modulator to the first camera such that the focal surface of the first camera is conjugate to a focal surface passing through the target.

2. The system of claim 1, wherein the refractive layer has a refractive index that varies substantially linearly with wavelength for wavelengths within a specified range of wavelengths.

3. The system of claim 1, wherein the target contains a fluorophore, and wherein the beam of illumination contains light at an excitation wavelength of the fluorophore.

4. The system of claim 1, wherein the optical system is configured to collimate the light emitted from the target in response to illumination that is directed toward the spatial light modulator.

5. The system of claim 1, further comprising:
a micromirror device, wherein the micromirror device comprises a substantially planar array of actuatable mirrors disposed on a surface, wherein respective angles of the actuatable mirrors relative to the surface are electronically controllable,
wherein the optical system is configured to direct the light from the light source to the target via reflection from a first set of one or more of the actuatable mirrors, and wherein the optical system is configured to direct the light emitted from the target in response toward the spatial light modulator via reflection from the first set of one or more actuatable mirrors such that the surface of the micromirror device is conjugate to the focal surface passing through the target, and
wherein the one or more actuatable mirrors in the first set have a first angle relative to the surface of the micromirror device.

6. The system of claim 1, further comprising:
a second camera, wherein the second camera comprises a plurality of light-sensitive elements disposed on a focal surface of the second camera;
a micromirror device, wherein the micromirror device comprises a substantially planar array of actuatable mirrors disposed on a surface, wherein respective angles of the actuatable mirrors relative to the surface are electronically controllable,
wherein the optical system is configured to direct the light from the light source to the target via reflection from a first set of one or more of the actuatable mirrors, wherein the optical system is configured to direct the light emitted from the target in response toward the second camera via reflection from the first set of one or more actuatable mirrors such that the surface of the micromirror device is conjugate to the focal surface passing through the target and such that the focal surface of the second camera is conjugate to a focal surface passing through the target, and wherein the optical system is configured to direct the light emitted from the target in response toward the spatial light modulator via reflection from a second set of one or more of the actuatable mirrors, and wherein the one or more actuatable mirrors in the first set have a first angle relative to the surface of the micromirror device and the one or more actuatable mirrors in the second set have a second angle relative to the surface of the micromirror device that is different from the first angle.

7. The system of claim 1, further comprising an actuated stage, wherein the actuated stage is configured to control the location of the target relative to the optical system.

8. The system of claim 1, wherein the spatial light modulator comprises an array of cells having respective electronically controllable refractive indexes.

9. A method comprising:
illuminating, by a light source, a target, via an optical system configured to direct light from the light source to the target;
electronically controlling a spatial light modulator during a first period of time such that a refractive layer of the spatial light modulator has a refractive index that varies spatially across the spatial light modulator according to a controllable gradient, wherein the controllable gradient has at least a first specified direction and a first specified magnitude, wherein the spatial light modulator further comprises a reflective layer disposed beneath the refractive layer, and wherein the refractive layer is chromatically disperse;
imaging light emitted from the target in response to the light from the light source during the first period of time using a first camera to produce a first image of the target, wherein the first camera comprises a plurality of light-sensitive elements disposed on a focal surface of the first camera, wherein the optical system is further configured to direct light emitted from the target in response to the light from the light source toward the spatial light modulator and direct light emitted from the target and reflected from the spatial light modulator to the first camera such that the focal surface of the first camera is conjugate to a focal surface passing through the target; and
determining spectrographic information for a particular region of the target based at least on the first image of the target.

10. The method of claim 9, further comprising:
electronically controlling the spatial light modulator during a plurality of further periods of time such that the refractive index of the refractive layer varies spatially across the spatial light modulator according to respective controllable gradients having at least respective specified directions and respective specified magnitudes; and
imaging light emitted from the target in response to the light from the light source during the plurality of further periods of time using the first camera to produce respective further images of the target, wherein determining spectrographic information for a particular region of the target comprises determining spectrographic information based on the first image and the plurality of further images of the target.

11. The method of claim 9, further comprising:
controlling a spectral resolution of the spectrographic information for the particular region of the target by controlling the first specified magnitude of the controllable gradient.

12. The method of claim 11, wherein the target contains a fluorophore, wherein a property of an emission spectrum of the fluorophore is related to a property of the target, wherein controlling a spectral resolution of the spectrographic information comprises controlling the spectrographic resolution to be sufficiently high to determine the property of the target based on determined spectrographic information for the particular region of the target.

13. The method of claim 11, wherein the target contains two fluorophores, wherein the two fluorophores have respective different emission spectra, wherein controlling a spectral resolution of the spectrographic information comprises controlling the spectrographic resolution to be sufficiently high to determine whether the particular region of the target contains the first fluorophore or the second fluorophore based on determined spectrographic information for the particular region of the target.

14. The method of claim 9, wherein the target contains a fluorophore, and wherein illuminating the target comprises emitting light at an excitation wavelength of the fluorophore.

15. The method of claim 9, further comprising:
operating a micromirror device to electronically control respective angles of actuatable mirrors of the micromirror device relative to a surface during the first period of time, wherein the actuatable mirrors comprise a substantially planar array and are disposed on the surface, and wherein operating the micromirror device to electronically control respective angles of actuatable mirrors of the micromirror device comprises controlling a first set of one or more of the actuatable mirrors to have a first angle relative to the surface of the micromirror device during a specified period of time during the first period of time, and
wherein the optical system is configured to direct the light from the light source to the target via reflection from the first set of one or more actuatable mirrors, and wherein the optical system is configured to direct the light emitted from the target in response toward the spatial light modulator via reflection from the first set of one or more actuatable mirrors such that the surface of the micromirror device is conjugate to the focal surface passing through the target.

16. The method of claim 15, wherein operating the micromirror device to electronically control respective angles of actuatable mirrors of the micromirror device relative to a surface comprises controlling the first set of at least one of the actuatable mirrors to have the first angle relative to the surface of the micromirror device during the first period of time, and wherein determining spectrographic information for a particular region of the target based at least on the first image of the target comprises determining spectrographic information for a portion of the target corresponding to the first set of one or more actuatable mirrors based on information in the first image detected by light-sensitive elements of the first camera located proximate to a portion of the focal surface of the first camera corresponding to the portion of the target.

17. The method of claim 9, further comprising:
operating a micromirror device to electronically control respective angles of actuatable mirrors of the micromirror device relative to a surface during the first period of time, wherein the actuatable mirrors comprise a substantially planar array and are disposed on the surface, and wherein operating the micromirror device to electronically control respective angles of actuatable mirrors of the micromirror device comprises controlling a first set of one or more of the actuatable mirrors to have a first angle relative to the surface during a specified period of time during the first period of time and controlling a second set of one or more of the actuatable mirrors to have a second angle relative to the surface during a specified period of time during the first period of time;

imaging light emitted from the target in response to the light from the light source during the first period of time using a second camera to produce a second image of the target, wherein the second camera comprises a plurality of light-sensitive elements disposed on a focal surface of the second camera, wherein the optical system is further configured to direct light emitted from the target in response to the light from the light source to the second camera such that the focal surface of the second camera is conjugate to the focal surface passing through the target; and wherein the optical system is configured to direct the light from the light source to the target via reflection from the first set of one or more actuatable mirrors, wherein the optical system is configured to direct the light emitted from the target in response toward the second camera via reflection from the first set of one or more actuatable mirrors and toward the spatial light modulator via reflection from the second set of one or more actuatable mirrors such that the surface of the micromirror device is conjugate to the focal surface passing through the target.

18. The method of claim 17, wherein operating the micromirror device to control respective angles of actuatable mirrors of the micromirror device during the first period of time comprises controlling, during respective specified periods of time during the first period of time: (i) a plurality of respective first sets of one or more actuatable mirrors to have the first angle relative to the surface and (ii) a plurality of respective second sets of one or more actuatable mirrors to have the second angle relative to the surface, and further comprising:

electronically controlling the spatial light modulator during a plurality of further periods of time such that the refractive index of the refractive layer varies spatially across the spatial light modulator according to respective controllable gradients having at least respective specified directions and respective specified magnitudes;

imaging light emitted from the target in response to the light from the light source during the plurality of further periods of time using the second camera to produce respective further images of the target; and imaging light emitted from the target in response to light from the light source during the plurality of further periods of time using the first camera to produce respective further images of the target, wherein determining spectrographic information for a particular region of the target comprises determining spectrographic information based on the first image and the plurality of further images of the target generated by the first camera.

19. The method of claim 9, further comprising:

controlling, using an actuated stage, the location of the target relative to the optical system.

20. The method of claim 9, wherein the spatial light modulator comprises an array of cells having respective electronically controllable refractive indexes, and wherein electronically controlling a spatial light modulator during a first period of time such that a refractive layer of the spatial light modulator has a refractive index that varies spatially across the spatial light modulator according to a controllable gradient comprises electronically controlling the refractive indexes of the cells such that refractive indexes of the cells vary in a direction corresponding to the first specified direction and at a spatial rate of change corresponding to the first specified magnitude.

* * * * *